(12) United States Patent
Sepetov et al.

(10) Patent No.: US 6,625,546 B2
(45) Date of Patent: Sep. 23, 2003

(54) STRUCTURE IDENTIFICATION METHODS USING MASS MEASUREMENTS

(75) Inventors: Nikolai F. Sepetov, Los Gatos, CA (US); Olga L. Issakova, Los Gatos, CA (US)

(73) Assignee: Nanoscale Combinatorial Synthesis, Inc., Mountain View, CA (US)

( * ) Notice: Subject to any disclaimer, the term of this patent is extended or adjusted under 35 U.S.C. 154(b) by 81 days.

(21) Appl. No.: 09/776,184

(22) Filed: Feb. 2, 2001

(65) Prior Publication Data

US 2002/0051999 A1 May 2, 2002

Related U.S. Application Data

(60) Provisional application No. 60/180,115, filed on Feb. 3, 2000, provisional application No. 60/180,111, filed on Feb. 3, 2000, provisional application No. 60/180,112, filed on Feb. 3, 2000, and provisional application No. 60/188,937, filed on Mar. 10, 2000.

(51) Int. Cl.$^7$ .................... G06F 19/00; G01N 33/48; G11C 17/00
(52) U.S. Cl. ................ 702/19; 702/23; 702/27; 365/94; 700/1
(58) Field of Search .................... 702/19, 23, 27; 70/1; 365/94

(56) References Cited

U.S. PATENT DOCUMENTS

| | | | |
|---|---|---|---|
| 4,631,211 A | | 12/1986 | Houghten |
| 5,727,213 A | * | 3/1998 | Vander Kamp et al. |
| 5,910,655 A | | 6/1999 | Skilling |
| 6,017,693 A | | 1/2000 | Yates, III et al. |
| 6,147,344 A | | 11/2000 | Annis et al. |
| 6,207,370 B1 | | 3/2001 | Little et al. |
| 6,207,861 B1 | | 3/2001 | Nash et al. |

FOREIGN PATENT DOCUMENTS

| | | |
|---|---|---|
| WO | WO 97/08190 A2 | 3/1997 |
| WO | WO 97/37953 A1 | 10/1997 |

OTHER PUBLICATIONS

Blom Strategies and Data Precision Requirements for the Mass Spectrometric Determination of Structures from Combinatorial Mixtures Anal. Chem. vol. 69 pp. 4353–4362 (1997).*

Dongre et al. Emerging tandem–mass–spectrometry techniques for the rapid identification of proteins, Trends in Biotechnology vol. 15 pp. 418–425 (1997).*

Boutin et al. Combinatorial Peptide Libraries: Robotic Synthesis and Analysis by Nuclear Magnetic Resonance, Mass spectroetry . . . Analytical Biochemistry vol. 234 pp. 126–141 (1996).*

Cargill and Maiefski (1996) "Automated combinatorial chemistry on solid phase," *Lab. Robotics. Automation* 8:139–148.

Castelino et al. (2000) "Automated sample storage for drug discovery," *Chim. Oggi.* 17:32–35.

Groger et al. (2000) "1,3,5–Triazines, versatile industrial building blocks: Synthetic approaches and applications," *Chim. Oggi.* 18:12–16.

Berlin et al. (1997) "Spectrometrically Monitored Selection Experiments–Quantitative Laser Desorption Mass Spectrometry of Small Chemical Libraries," *Chem. Biol.* 4:63–77.

Brummel et al. (1996) "Evaluation of Mass Spectrometric Methods Applicable to the Direct Analysis of Non–Peptide Bead–Bound Combinatorial Libraries," *N. Anal. Chem.* 68:237–242.

Bunin and Ellman (1992) "A general and expedient method for the solid phase synthesis of 1,4–benzodiazepine derivatives," *J. Amer. Chem. Soc.* 114:10997–10998.

Bunin et al. (1994) "The combinatorial synthesis and chemical and biological evaluation of 1,4–benzodiazepine library," *Proc. Natl. Acad. Sci. USA* 91:4708–4712.

Carrasco et al. (1997) "Direct Monitoring of Organic Reactions on Polymeric Supports," *Tetrahedron Lett.* 38:6331–6334.

Chu et al. (1993) "Using affinity capillary electrophoresis to identify the peptide in a peptide library that binds most tightly to vancomycin," *J. Org. Chem.* 58:648–652.

Davis and Swayze (2000) "Automated solid–phase synthesis of linear nitrogen–linked compounds," *Biotechnol. Bioeng.* 71:19–27.

Demirev and Zubarev (1997) "Probing combinatorial library diversity by mass spectrometry," *Anal. Chem.* 69:2893–2900.

(List continued on next page.)

*Primary Examiner*—John S. Brusca
(74) *Attorney, Agent, or Firm*—Christopher C. Sappenfield; Jonathan Alan Quine; Quine Intellectual Property Law Group, P.C.

(57) ABSTRACT

Methods of identifying predicted or actual structures of members of a chemical or physical library are provided. The methods provide for the direct identification of compound structure following combinatorial synthesis using molecular mass measurements of individual compounds, thereby eliminating the necessity of encoding synthetic steps. The analysis of mass spectrometric data for sets of related compounds reveals compounds that are missing in a group of related compounds and identifies compounds that do not belong to a group of related compounds due to unexpected chemical, physical, or biological transformations. The methods may be applied to any group of compounds originating from chemical reactions where one reactant is common to the synthetic transformation. One particular application of these methods is in the analysis of the products of combinatorial synthesis. Systems, computer programs products, and kits are additionally provided.

81 Claims, 14 Drawing Sheets

OTHER PUBLICATIONS

Enjalbal et al., (2000) "Mass spectrometry in combinatorial chemistry," *Mass Spectrom. Rev.* 19:139–161.

Fitch et al. (1994) "High–resolution (1) H NMR in solid–phase organic synthesis," *J. Org. Chem.* 59:7955–7956.

Gao et al. (1996) "Screening derivatized peptide libraries for tight binding inhibitors to carbonic anhydrase II by electrospray ionization mass spectrometry," *J. Med. Chem.* 39:1949–1955.

Hagg (2000) "Chemspeed Ltd.: Automated and unattended parallel synthesis integrating work–up and analysis," *Chimia* 54:163–164.

Haap et al. (1998) "FT–IR Mapping—A New Tool for Spatially–Resolved Characterization of Polymer–Bound Combinatorial compound Libraries with Ir Microscopy," *Angew. Chem. Int. Ed.* 37(23):3311–3314.

Houghten (1985) "General method for the rapid solid–phase synthesis of large numbers of peptides," *Proc. Natl. Acad. Sci. USA* 82:5131–5135.

Houghten et al. (1991) "Generation and use of synthetic peptide combinatorial libraries for basic research and drug discovery" *Nature* 354:84–86.

Hu et al. (2000) "Automated solid–phase synthesis and photophysical properties of oligodeoxynucleotides labeled at 5'–aminothymidine with Ru(bpy)(2)(4–m–4'–cam–bpy)(2+)," *Inorg. Chem.* 39:2500–2504.

Hudson (1999) "Matrix–assisted synthetic transformations: a mosaic of different contributions. 1. The pattern emerges," *J. Comb. Chem.* 1:330–360.

Hughes (1998) "Design of self–coded combinatorial libraries to facilitate direct analysis of ligands by mass spectrometry," *J. Med.Chem.* 41:3804–3811.

Keifer (1996) "Influence of resin structure, tether length, and solvent upon the high–resolution (1)H NMR spectra of solid–phase–synthesis resins," *J. Org. Chem.* 61:1558–1559.

Keifer et al. (2000) "Direct–injection NMR (DI–NMR): A flow NMR technique for the analysis of combinatorial chemistry libraries," *Journal of Combinatorial Chemistry* 2; 151–171.

Konings et al. (1996) "Deconvolution of combinatorial libraries for drug discovery: theoretical comparison of pooling strategies," *J. Med. Chem.* 39: 2710–2719.

Lake et al. (2000) "Sample Preparation for high throughput accurate mass analysis by matrix–assisted laser desorption/ionization time–of–flight mass spectrometry," *Rapid Commun. Mass Spectrom.* 14:1008–1013.

Lewis et al. (2000) "Automated high–throughput quantification of combinatorial arrays," *American Pharmaceutical Review* 3:63–68.

McGregor and Muskal (1999) "Pharmocophore fingerprinting 1. application to QSAR and focused library design," *J. Chem. Inf. Comput. Sci.* 39:569–574.

Meldal (1992) "PEGA: A flow stable polyethylene glycol dimethyl acryamide copolymer for solid phase synthesis," *Tetrahedron Lett.* 33:3077.

Metzger et al. (1993) "Ion–spray mass spectrometry and high–performance liquid chromatography. Mass spectrometry of synthetic peptide libraries," *Angew. Chem. Int. Ed.* 32:894–896.

Newcomb et al. (1998) "Analysis of 9–fluorenylmethoxycarbonyl (Fmoc) loading of solid–phase synthesis resins by gas chromatography," *Biotech. Bioeng.* (Comb. Chem.) 61:55–60.

North (2000) "Implementation of analytical technologies in a pharmaceutical development organization–looking into the next millennium," *Journal of Automated Methods and Management in Chemistry* 22:41–45.

Pickett et al. (1998) "Strategies for the design and comparison of combinatorial libraries using pharmacophoric descriptors," *J. Chem. Inf. Comput. Sci.* 38:144–150.

Schriemer et al. (1998) "Microscale Frontal Affinity–Chromatography with Mass–Spectrometric Detection—A New Method for the Screening of Compound Libraries," *Angew. Chem. Int. Ed.* 37(24):3383–3387.

Sheridan and Kearsley (1995) "Using a genetic algorithm to suggest combinatorial libraries," *J. Chem. Inf. Comput. Sci.* 35:310–320.

Sherrington (1998) "Preparation, structure, and morphology of polymer supports," *Chem. Commun.* 2275–2286.

Stevanovic and Jung (1993) "Multiple sequence analysis: Pool sequencing of synthetic and natural peptide libraries," *Anal. Biochem.* 212:212–220.

van Breemen et al. (1997) "Pulsed ultrafiltration mass spectrometry: A new method for screening combinatorial libraries," *Anal. Chem.* 69:2159–2164.

Wilson–Lingardo et al. (1996) "Deconvolution of combinatorial libraries for drug discovery: experimental comparison of pooling strategies," *J. Med. Chem.* 39:2720–2726.

Youngquist et al. (1994) "Matrix–assisted laser desorption ionization for rapid determination of the sequences of biologically active peptides isolated from support–bound combinatorial peptide libraries," *Rapid Commun. Mass Spectrom.* 8:77–81.

Zuckermann et al. (1992) "Design, construction and application of a fully automated equimolar peptide mixture synthesizer," *Int. J. Peptide Prot. Res.* 40: 497–506.

* cited by examiner

A1 correlate mass measurements of two or more library members having a shared chemical history with two or more virtual masses in the logical matrix to identify one or more groups of virtual masses that most likely describe transformations undergone by the two or more library members

A2 identify the structures of the two or more chemical or physical library members within the one or more identified groups based on the mass measurements

| calculate matrix entries (ME) by separately summing masses for each member $a$ of an initial set $\{a\}$ with each mass change $\Delta M$ in a set of expected mass changes $\{\Delta M_{exp}\}$ |

A2

| assign each ME to one of $m$ groups, where $m$ corresponds to a total number $\Delta M$s in $\{\Delta M_{exp}\}$, and in which each $m$ group includes $n$ members, where $n$ corresponds to a total number of $a$s in $\{a\}$ |

A3

| match a selected $b$ mass from $\{b\}$ with all identical ME and exclude any of the $m$ groups lacking a member $n$ with a mass identical the selected $b$ mass from further consideration to reduce the number of $m$ groups available for subsequent consideration |

A4

| repeat A3 at least once, in which each repeated A3 includes matching a different selected $b$ mass from $\{b\}$ with all the identical ME that remain in the reduced number of $m$ groups from an immediately preceding A3 and excluding any of the reduced number of $m$ groups lacking an $n$ member with a mass identical to the different selected $b$ mass from further consideration to further reduce the number of $m$ groups available for subsequent consideration |

A5

RESULTS:

identify a single $m$ group which indicates that matched selected $b$ masses from $\{b\}$ have a shared chemical history or identify more than one $m$ group for further consideration which indicates that insufficient data exists for an unambiguous determination of whether selected $b$ masses from $\{b\}$ have a shared chemical history or identify no $m$ group for further consideration which indicates that selected $b$ masses from $\{b\}$ originate from materials lacking a shared chemical history

Fig. 2

A1
calculate matrix entries (ME) by separately summing masses for each member $a$ of an initial set $\{a\}$ with each mass change $\Delta M$ in a set of expected mass changes $\{\Delta M_{exp}\}$

A2
assign each ME to one of $m$ groups, where $m$ corresponds to a total number $\Delta M$s in $\{\Delta M_{exp}\}$, and in which each $m$ group includes $n$ members, where $n$ corresponds to a total number of $a$ in $\{a\}$

A3
assign each of the $m$ groups a $P$ variable in which each $P$ is initially zero

A4
match a selected $b$ mass from $\{b\}$ with identical ME in each of the $m$ groups in which the $P$ for an $m$ group is increased by one when a match occurs

A5
repeat A4 for each remaining $b$ mass from $\{b\}$

A6
determine which one or more $m$ groups have highest $P$s to identify one or more $\Delta M$s in $\{\Delta M_{exp}\}$ best fitting $\{b\}$, and all paired values in $\{a\}$ and $\{b\}$ with a shared chemical history

Fig. 3

A1 determine masses for each $x$ member of a synthesized library $\{b_x\}$ in which each $b$ is derived from a member $a$ of an initial set $\{a\}$ and has a shared chemical history with all other members of $\{b_x\}$

A2 subtract a total mass of $\{a\}$ from a total mass of $\{b_x\}$ to determine a total mass change $\Delta M_{tot}$ of $\{b_x\}$

A3 divide $\Delta M_{tot}$ by $x$ to determine a mass change $\Delta M_x$ for each $b$ of $\{b_x\}$

A4 subtract $\Delta M_x$ from each $b$ of $\{b_x\}$ to identify each $a$ of $\{a\}$ corresponding to each $b$

Fig. 4

A1 calculate matrix entries (*ME*) by separately summing masses for each member $a$ of an initial set $\{a\}$ with each mass change $\Delta M$ in a set of expected mass changes $\{\Delta M_{exp}\}$

A2 assign each *ME* to one of $n$ groups, where $n$ corresponds to a total number of $a$ in $\{a\}$ and in which each $n$ group includes $m$ members, where $m$ corresponds to a total number $\Delta Ms$ in $\{\Delta M_{exp}\}$

A3 match a selected $b$ mass from $\{b\}$ with all identical *ME* and exclude any of the $n$ groups lacking a member $m$ with a mass identical the selected $b$ mass from further consideration to reduce the number of $n$ groups available for subsequent consideration

A4 repeat A3 at least once, in which each repeated A3 includes matching a different selected $b$ mass from $\{b\}$ with all the identical *ME* that remain in the reduced number of $n$ groups from an immediately preceding A3 and excluding any of the reduced number of $n$ groups lacking an $m$ member with a mass identical to the different selected $b$ mass from further consideration to further reduce the number of $n$ groups available for subsequent consideration

A5

RESULTS:

identify a single $n$ group which indicates that matched selected $b$ masses from $\{b\}$ have a shared initial mass or identify more than one $n$ group for further consideration which indicates that insufficient data exists for an unambiguous determination of whether selected $b$ masses from $\{b\}$ have a shared initial mass or identify no $n$ group for further consideration which indicates that selected $b$ masses from $\{b\}$ originate from materials lacking a shared initial mass

Fig. 5

A1 calculate matrix entries ($ME$) by separately summing masses for each member $a$ of an initial set $\{a\}$ with each mass change $\Delta M$ in a set of expected mass changes $\{\Delta M_{exp}\}$

A2 assign each $ME$ to one of $n$ groups, where $n$ corresponds to a total number of $a$ in $\{a\}$ and in which each $n$ group includes $m$ members, where $m$ corresponds to a total number $\Delta Ms$ in $\{\Delta M_{exp}\}$

A3 assign each of the $n$ groups a $Q$ variable in which each $Q$ is initially zero

A4 match a selected $b$ mass from $\{b\}$ with identical $ME$ in each of the $n$ groups in which the $Q$ for an $n$ group is increased by one when a match occurs

A5 repeat A4 for each remaining $b$ mass from $\{b\}$

A6 determine which one or more $n$ groups have highest $Q$s to identify one or more masses $a$ from $\{a\}$ best fitting $\{b\}$, and all paired values in $\{a\}$ and $\{b\}$ with a shared initial mass

Fig. 6

STRUCTURE IDENTIFICATION METHODS USING MASS MEASUREMENTS

CROSS-REFERENCES TO RELATED APPLICATIONS

This application is related to U.S. Ser. No. 60/180,115 entitled "STRUCTURE DETERMINATION METHODS USING MASS MEASUREMENT," by Sepetov et al., filed Feb. 3, 2000; U.S. Ser. No. 60/180,111 entitled "NONREDUNDANT SPLIT POOL SYNTHESIS OF COMBINATORIAL LIBRARIES," by Sepetov et al., filed Feb. 3, 2000; U.S. Ser. No. 60/180,112 entitled "SYNTHETIC METHODS TO CREATE A SHARED CHEMICAL HISTORY," by Sepetov et al., filed Feb. 3, 2000; and U.S. Ser. No. 60/188,937 entitled "NEW SYNTHETIC METHODS TO CREATE A SHARED CHEMICAL HISTORY," by Sepetov et al., filed Mar. 10, 2000. Each of these prior applications is incorporated herein by reference in its entirety for all purposes. The present application claims priority to and the benefit of these related applications pursuant to 35 U.S.C. §119(e), as well as any other applicable statute or rule.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

1. Field of the Invention

The field of this invention relates to mass spectrometry and the analysis of data obtained by mass spectrometry, e.g., including analysis of combinatorial libraries by mass spectrometry.

2. Description of the Related Art

Mass spectrometry is one of the most universal and sensitive analytical methods for compound characterization. Every chemical compound has a molecular mass and, typically, only a minute quantity of analyte is necessary to obtain a mass measurement. These features make mass spectrometry a method of choice for analyzing the products of combinatorial synthetic chemistry.

In comparison with information-rich methods, such as nuclear magnetic resonance (NMR), mass spectrometry measurements have low information content. Many compounds with different chemical structures may have the same molecular weight or the same mass-to-charge ratio. This limits the utility of mass spectrometry for structural identification, especially in combinatorial chemistry where large numbers of compounds are frequently synthesized using a common scaffold and sets of related reagents to produce synthetic products with a narrow distribution of molecular masses. Most often, mass spectrometry is used to confirm an expected chemical structure, or is used in combination with other information to help identify the structure of unknown compounds.

The information content of mass spectrometry may be increased through the use of multistage mass spectrometry (i.e., mass measurement of ions obtained by fragmenting molecules of interest) or accurate mass measurements. However, interpreting data obtained by multistage mass spectrometry requires knowledge of fragmentation pathways for the molecules being analyzed, which is usually not available a priori. Application of accurate mass measurements is limited by the existence of many compounds with the same elemental composition, in which case, increasing the accuracy of measurement does not provide additional information. The expense and sophistication of the hardware required for both multistage and accurate mass measurement as well as the limited capacity of these instruments for high throughput measurement further restrict their application in the analysis of the products of combinatorial chemistry.

Thus, there is a substantial need for new methods and related systems that provide more efficient use of mass spectrometry for structural identification, especially for combinatorial chemistry-related applications.

SUMMARY OF THE INVENTION

The present invention includes a method of identifying predicted or actual structures of two or more members of a chemical or physical library. In preferred embodiments, the method is completely or partially computer implemented. The method includes (a) providing a logical matrix that includes virtual masses of members of a complex library (e.g., a combinatorial chemical library or the like) produced by chemical or physical transformations of an initial set of chemical or physical members (e.g., an initial set of building blocks or the like) in which at least one group of the virtual masses includes complex library members having a shared chemical history. The method also includes (b) correlating molecular mass measurements (e.g., mass spectrometric measurements) of two or more chemical or physical library members (e.g., members of a combinatorial synthetic library) having a shared chemical history with two or more virtual masses in the logical matrix to identify one or more groups of virtual masses that most likely describe chemical or physical transformations undergone by the two or more chemical or physical library members. In certain embodiments, the one or more groups of virtual masses describe (i.e., definitively) the chemical or physical transformations undergone by the two or more chemical or physical library members in (b). Additionally, the correlations in (b) generally account for one or more mass defects of reaction. Finally, the method includes (c) identifying the predicted or actual structures of the two or more chemical or physical library members within the one or more identified groups based one the molecular mass measurements.

In some embodiments, (a) includes calculating individual masses for each member of the logical matrix by separately summing masses for each member of the initial set of chemical or physical members with each mass in a set of expected mass changes. In certain embodiments, the set of expected mass changes includes a set of virtual mass changes calculated by separately subtracting masses for each member of the initial set of chemical or physical members from each mass in the set of chemical or physical library members. Each calculated individual mass is assigned to one of m groups, m corresponding to a total number of individual mass changes in the set of expected mass changes. Furthermore, each of the m groups includes n members, n corresponding to a total number of members in the initial set of chemical or physical members.

Optionally, (b) includes (i) matching a selected mass from the set of chemical or physical library members with all identical calculated masses and excluding any of the m groups lacking a member n comprising a mass identical to the selected mass from further consideration to reduce a number of m groups available for subsequent consideration.

Thereafter, the method typically includes (ii) repeating (i) at least once, in which each repeated (i) includes matching a different selected mass from the set of chemical or physical library members with all the identical calculated masses that remain in the reduced number of m groups from an immediately preceding (i) and excluding any of the reduced number of m groups lacking an n member with a mass identical to the different selected mass from further consideration to further reduce the number of m groups available for subsequent consideration. This method leads to (1) identifying a single m group which indicates that matched masses from the set of chemical or physical library members have a shared chemical history, (2) identifying more than one m group for further consideration which indicates that insufficient data exists for an unambiguous determination of whether masses selected from the set of chemical or physical library members have a shared chemical history, or (3) identifying no m group for further consideration which indicates that masses selected from the set of chemical or physical library members originate from materials lacking a shared chemical history.

In certain embodiments, the method further includes assigning each of the m groups a P variable in which each P variable is typically initially zero. In these embodiments, (b) includes (i) matching a selected mass from the set of chemical or physical library members with identical masses in each of the m groups in which the P variable for an m group is increased by one when the selected mass matches at least one value therein. Thereafter, these embodiments include (ii) repeating (i) for each remaining value in the set of chemical or physical library members, and (iii) determining which one or more m groups have highest P variables to identify one or more mass changes from the set of expected mass changes best fitting the set of chemical or physical library members. It also identifies all paired values in the initial set of chemical or physical members and the set of chemical or physical library members originating from materials with a shared chemical history.

In certain aspects of the invention, (a) includes solving a simultaneous system of equations to provide one or more values in the logical matrix. For example, solving the simultaneous system of equations optionally includes solving for one or more masses of one or more members of the initial set of chemical or physical members. Optionally, solving the simultaneous system of equations includes solving for one or more of: at least one mass of at least one member of the set of chemical or physical library members, at least one mass of at least one of the initial set of chemical or physical members, or at least one member of a set of expected mass changes.

In one embodiment, (b) includes (i) determining the molecular mass measurements for each of x members of a set of chemical or physical library members, wherein x is at least two, and wherein each x member is derived from one member of the initial set of chemical or physical members and comprises a shared chemical history with all other x members. This embodiment also includes (ii) subtracting a cumulative total mass of all members of the initial set of chemical or physical members from a cumulative total mass of all x members of the set of chemical or physical library members to determine a cumulative total mass change for the set of chemical or physical library members and (iii) dividing the cumulative total mass change by x to thereby determine a mass change for each of the x members of the set of chemical or physical library members. In addition, this embodiment includes (iv) subtracting the mass change of (iii) from each of the molecular mass measurements of (i) to identify each member in the initial set of chemical or physical members corresponding to each individual x member of the set of chemical or physical library members.

The present invention also relates to a system for identifying predicted or actual structures for two or more members of a chemical or physical library. The system includes (a) at least one computer that includes a database having a logical matrix, or data structure including virtual masses of members of a complex library produced by chemical or physical transformations of an initial set of chemical or physical members in which at least one group of the virtual masses comprises complex library members having a shared chemical history. The system also includes (b) system software that includes one or more logic instructions for (i) correlating molecular mass measurements of two or more chemical or physical library members having a shared chemical history with two or more virtual masses in the logical matrix to identify one or more groups of virtual masses that most likely describe chemical or physical transformations undergone by the two or more chemical or physical library members. The correlations in (i) generally account for one or more mass defects of reaction. The system software also includes one or more logic instructions for (ii) identifying the predicted or actual structures of the two or more chemical or physical library members within the one or more identified groups based on the molecular mass measurements. In some embodiments, the one or more groups of virtual masses describe (i.e., definitively) the chemical or physical transformations undergone by the two or more chemical or physical library members in (b).

The system typically further includes a mass spectrometer operably connected to the at least one computer which provides the molecular mass measurements to be correlated. In addition, the system generally includes a handling system (e.g., a solid support handler, such as a bead handler, a bead container handler, a reagent handler, or the like) operably connected to the at least one computer, which handling system directs translocation and synthesis of the chemical or physical library members. The handling system generally includes at least one robotic armature.

The present invention additionally provides a computer program product that includes a computer readable medium having one or more logic instructions for (a) correlating molecular mass measurements of two or more chemical or physical library members having a shared chemical history with two or more virtual masses in a logical matrix or data structure to identify one or more groups of virtual masses that most likely describe chemical or physical transformations undergone by the two or more chemical or physical library members. The computer program product also includes one or more logic instructions for (b) identifying predicted or actual structures of the two or more chemical or physical library members within the one or more identified groups based one the molecular mass measurements. The correlations optionally account for or determine one or more mass defects of reaction. The computer readable medium optionally includes one or more of: a CD-ROM, a floppy disk, a tape, a flash memory device or component, a system memory device or component, a hard drive, a data signal embodied in a carrier wave, or the like.

The invention can also be embodied in kits, e.g., including any of the system elements for performing any of the methods described herein, and optionally, further including containers for holding any of the relevant system elements, packaging materials, instructional materials for practicing the methods, or the like.

BRIEF DESCRIPTION OF THE DRAWINGS

FIG. 1 is a flow chart that schematically shows steps involved in an embodiment of the structural identification method.

FIG. 2 is a flow chart that schematically shows steps involved in an embodiment of the invention for determining whether selected members from a final set of library members have a shared chemical history.

FIG. 3 is a flow chart that schematically shows steps involved in an embodiment of the structural identification method that utilizes P variables.

FIG. 4 is a flow chart that schematically shows steps involved in solving a system of equations to identify members of an initial of chemical or physical members corresponding to members in a set of chemical or physical library members.

FIG. 5 is a flow chart that schematically shows steps involved in an embodiment of the invention for determining whether selected members from a final set of library members have a shared initial mass.

FIG. 6 is a flow chart that schematically shows steps involved in an embodiment of the structural identification method that utilizes Q variables.

DEFINITIONS

Figure 7A:
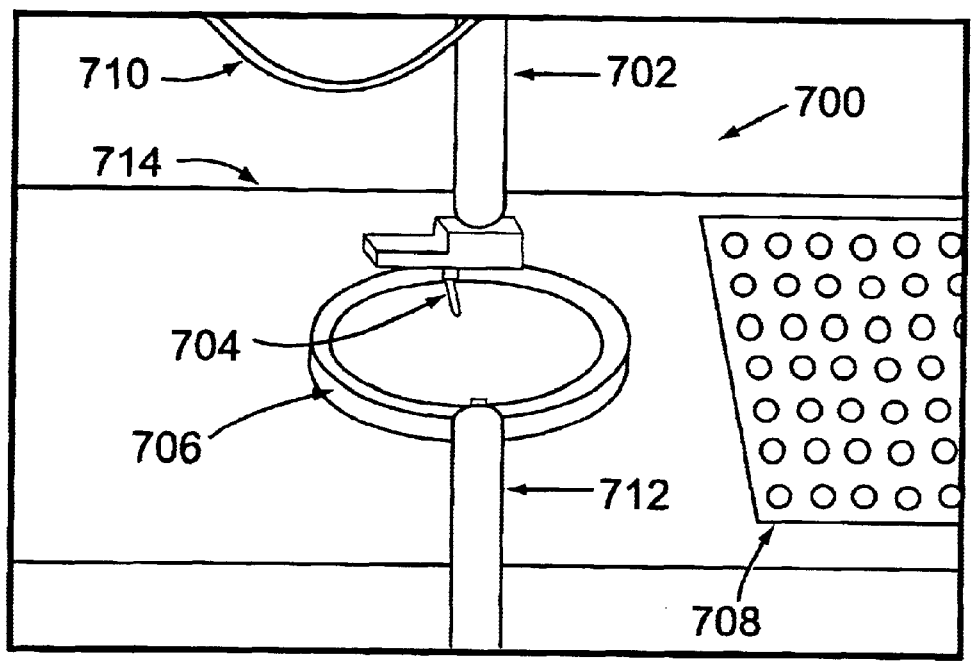
FIG. 7A schematically depicts certain aspects of a handling system.

Unless otherwise indicated, the following definitions supplement those in the art.

A "library" refers to a set of compounds or materials. A "combinatorial" library refers to a set of compounds or materials prepared by combinatorial chemistry. A library optionally includes a collection of pools or sub-libraries. A "sub-library" is a sub-set of compounds or materials, e.g., a collection of materials or compounds obtained from solid phase synthesis units, e.g., within a particular container or vessel in the methods described herein. A library "member" refers, e.g., to a specific material or compound that is included in a library, e.g., a characterized or uncharacterized physical product or material of a library synthesis. A "virtual" library refers to a representation of a physical library, such as a representation of the library in electronic or paper form. Members of a virtual library are optionally represented in essentially any physical or logical matrix. The building blocks utilized for such a library may or may not exist, and the chemical steps to form such a library may or may not have been tested. These virtual libraries are optionally used in the design and evaluation of possible physical/chemical libraries. See, e.g., Sheridan and Kearsley (1995) "Using a genetic algorithm to suggest combinatorial libraries," *J. Chem. Inf. Comput. Sci.* 35:310–320.

A "virtual mass" refers to a postulated or represented mass of a postulated or actual compound. For example, a virtual mass may include a summation of masses of building blocks, scaffolds, or other components to be used in the synthesis of a target compound whether the synthesis is actually performed or not. Similarly, a "virtual mass change" refers to a postulated or represented mass change of a compound.

A "data structure" or "logical matrix" refers to an ordered array of elements, such as a data table, e.g., including numerical, alphabetical, or mathematical elements (e.g., virtual or actual masses, simultaneous linear equations, or the like). For example, a logical matrix can include rows and columns of virtual masses of actual or postulated library members produced by chemical or physical transformations of, e.g., an initial set of chemical or physical members. A matrix entry can include, e.g., a sum of a mass of a member of an initial set of chemical or physical members and a mass change from a set of expected mass changes, a difference in mass between a chemical or physical library member and a mass of a member of an initial set of chemical or physical members, a mass of a member of an initial set of chemical or physical members, a mass of a chemical or physical library member, a mass change, a P variable, a Q variable, or any other data table entry. The matrix can also include organizational elements, such as column and/or row identifiers or the like.

A "chemical or physical transformation" refers to a chemical reaction or a sequence of chemical reactions, or a physical interaction (e.g., an ionic or other non-covalent interaction) or sequence of physical interactions, that change the structure or mass of, e.g., a library member.

An "initial set of chemical or physical members," "initial set of MW," "initial set of masses," "initial set of M," "($a_1$, $a_2$, . . . , $a_n$),"  where n is equal to the number of unique masses in the initial set), or simply "$\{a\}$" refers to values that are assumed, assigned, or postulated to be the masses or weights of a set of compounds before a given physical or chemical transformation. The values of the initial set of chemical or physical members should be, but are not necessarily, known. The values may be based on information about the reagents used to perform the chemical transformations, on measurements in mass spectrometry or other structure confirmatory experiments, or both. In the case where the values are determined directly by mass spectrometry, the values in the initial set of MW may result from either a compound present in the samples tested or may be the result of experimental errors. All values in an initial set of chemical or physical members can be, but are not necessarily, unique. In cases where some of the reagents have non-unique masses, additional information associated with the compounds may be used to differentiate them. Such information may include, but is not limited to, unusual isotopic distributions, substantial differences in retention times in liquid chromatography/mass spectrometry experiments, or the like.

A "final set of MW," "final set of M," "set of chemical or physical library members," "($b_1$, $b_2$, . . . , $b_p$)" where p equals the number of molecular weights in the final set, or simply "$\{b\}$" refers to values that are assumed to be the masses or weights of a set of compounds after chemical transformation. All the values in the set of chemical or physical library members can be, but are not necessarily, known from mass spectrometry measurements. Thus, some of the numbers in the set of chemical or physical library members may not originate from real compounds but may be the result of experimental error.

The term "Δmw," "ΔMW," "ΔM," or "mass change" refers to a difference between values in a final and an initial (or intermediate) set of Ms. In the case when these values are assigned to molecular masses or weights of a compound before and after one or more chemical transformation, ΔM is a change in the molecular mass or weight of a compound as a result of the chemical transformation(s).

A "set of expected Δmw," "set of expected ΔM," "set of expected mass changes," "($\Delta mw_1$, $\Delta mw_2$, . . . , $\Delta mw_m$,)" where m equals the number of expected Δmw, or simply "{$\Delta M_{exp}$}" refers to a set of expected differences in the molecular weight or mass of compounds prior to and following chemical transformation. All expected ΔMs in a set can be, but are not necessarily, different. In cases where some of the expected ΔMs in a set are equal, additional information associated with reagents causing chemical transformations are optionally used to differentiate these ΔMs values. Such additional information may include, but is not limited to, unusual isotopic distributions, substantial differences in retention times in liquid chromatography/ mass spectrometry experiments, or the like.

A set of compounds with a "shared chemical history" or "SCH" refers to a group of compounds that experience conditions that should produce a common chemical, biological, or physical transformation and change in molecular weight or mass for all compounds in the group.

A set of compounds with a "shared initial mass" or "SIM" refers to a group of compounds that originate from the same member of an initial set of chemical or physical members.

A "subset of an initial set of MW originating from compounds with a shared chemical history," or a "subset of an initial set of chemical or physical members originating from compounds with a shared chemical history" indicates that for each value in this subset of data there is a corresponding value in the final set of M such that the difference between these values is the same for all pairs of values corresponding to the subset.

A "subset of a final set of MW originating from compounds with a shared chemical history," or "subset of a set of chemical or physical library members originating from compounds with a shared chemical history" indicates that for each value in this subset of data there is a corresponding value in the initial set of chemical or physical members such that the difference between these values is the same for all pairs of values. In general, none, one, or more then one subset may be described as originating from compounds with a shared chemical history depending on the values obtained in measuring initial and final M for a set of compounds.

A "resin" refers to an insoluble material (e.g., a polymeric material) or particle which allows ready separation from liquid phase materials by filtration. Resins can be used to carry library members (e.g., solid supports) or reagents, or to trap excess reagents or reaction by-products, or the like. A "solid support" refers to an insoluble, functionalized, polymeric material or particle to which library members or reagents may be attached (e.g., via a linker) allowing them to be readily separated (by filtration, centrifugation, etc.) from excess reagents, soluble reaction by-products or solvents. Examples of solid supports suitable for the methods described herein include, e.g., glass supports, plastic supports, silicon supports, chips, beads, pins, filters, membranes, microwell plates, slides, or the like. See also, Sherrington (1998) "Preparation, structure, and morphology of polymer supports," *Chem. Commun.* 2275–2286, Winter "Supports for solid-phase organic synthesis," In *Combinatorial Peptide and Non-Peptide Libraries* (G. Jung, ed.), pp. 465–509. VCH, Weinheim (1996), and Hudson (1999) "Matrix-assisted synthetic transformations: a mosaic of different contributions. 1. The pattern emerges," *J. Comb. Chem.* 1:330–360. A solid support is "functionalized" when it includes a linker, a scaffold, a building block, or other reactive moiety attached thereto, whereas a solid support is "nonfunctionalized" when it lack such a reactive moiety.

A "solid phase synthesis unit" refers to a certain amount of material upon or in which a combinatorial synthesis is performed. Solid phase synthesis units optionally include, e.g., single particles of solid supports or resins such as beads, crowns, pieces of polymer, pieces of cellulose (paper, cotton, etc.), or the like. Solid phase synthesis units also optionally include, e.g., multiple particles combined together, e.g., which are not separated during combinatorial synthesis, such as a tea-bag or other porous container with beads, an array of solid supports, or the like. Containers such as tea-bags are discussed further in, e.g., Houghten (1985) "General method for the rapid solid-phase synthesis of large numbers of peptides," *Proc. Natl. Acad. Sci. USA* 82:5131–5135 and in U.S. Pat. No. 4,631,211 "MEANS FOR SEQUENTIAL SOLID PHASE ORGANIC SYNTHESIS AND METHODS USING THE SAME," issued Dec. 23, 1986 to Houghten. A "container" refers to a physical grouping of multiple solid phase supports. A "reaction vessel" refers to a vessel capable of containing solid phase synthesis units, whether present as single particles of solid supports or resins, or as multiple particles combined together in, e.g., a container. One type of reaction vessel is a "microwell plate," which is a substrate that includes a plurality of regions that retain one or more fluidic materials.

A "choice" refers to the alternative variables (e.g., combination of various different components or building blocks, etc.) for a given stage in a combinatorial synthesis. The term "stage" refers to a step in a sequential combinatorial synthesis of a compound or material.

A "building block" or "component" refers to one of a number of interchangeable reagents which are optionally used in combinatorial library synthesis, at least part of the structure of which becomes incorporated into an intermediate or final product. Building blocks or components may include a set of reagents that introduces diversity into library products and/or one that results in an identical conversion for each member of the library. A "scaffold" or "template" refers to a core portion of a molecule common to all members of a combinatorial library or sub-library.

A "linker" or "tether" refers to a bifunctional chemical moiety attaching a compound to, e.g., a solid support which can be cleaved to release materials or compounds from the support. A careful choice of linker allows cleavage to be performed under appropriate conditions compatible with the stability of the compound and assay method. Additional description of linker molecules is provided in, e.g., Backes and Ellman (1997) "Solid support linker strategies," *Curr. Opin. Chem. Biol.* 1:86–93, Backes et al. (1996) "Activation method to prepare a highly reactive acylsulfonamide "safety-catch" linker for solid-phase synthesis," *J. Amer. Chem. Soc.* 118:3055–3056, Backes and Ellman (1994) "Carbon-carbon bond-forming methods on solid support. Utilization of Kenner's "Safety-Catch" linker," *J. Amer. Chem. Soc.* 116:11171–11172, Hoffmann and Frank (1994) "A new safety-catch peptide-resin linkage for the direct release of peptides into aqueous buffers," *Tetrahedron Lett.* 35:7763–7766, Kocis et al. (1993) "Symmetrical structure allowing the selective multiple release of a defined quantity of peptide from a single bead of polymeric support," *Tetrahedron Lett.* 34:7251–7252, and Plunkett and Ellman (1995) "A silicon-based linker for traceless solid-phase synthesis," *J. Org. Chem.* 60:6006–6007.

The term "cleavage" refers to a process of releasing a material or compound from a solid support, e.g., to permit analysis of the compound by solution-phase methods. See, e.g., Wells et al. (1998) "Cleavage and Analysis of Material from Single Resin Beads," *J. Org. Chem.* 63:6430–6431.

A "set" includes a group or a collection of at least two solid phase synthesis units, virtual or actual masses, components, synthesis products, particles, or other materials.

"Deconvolution" refers to a process of rendering, e.g., a combinatorial library less complex and/or of identifying or characterizing one or more members of the library. The process optionally includes identifying the structure of a particular library member. Optionally, the process includes optimizing an activity of interest by, e.g., fractionating (e.g., by resynthesis, or by elaborating a partial library) a pool with some level of the desired activity to give a set of smaller pools. Repetition of this strategy (i.e., "iterative deconvolution") ideally leads to single members with a high level of activity. Additional details regarding combinatorial library deconvolution are described in, e.g., Houghten et al. (1991) "Generation and use of synthetic peptide combinatorial libraries for basic research and drug discovery" *Nature* 354:84–86, Konings et al. (1996) "Deconvolution of combinatorial libraries for drug discovery: theoretical comparison of pooling strategies," *J. Med. Chem.* 39:2710–2719, and Wilson-Lingardo et al. (1996) "Deconvolution of combinatorial libraries for drug discovery: experimental comparison of pooling strategies," *J. Med. Chem.* 39:2720–2726.

A "mass defect of reaction" is a portion or deficiency of a detected mass of a given library member that is not attributable to the predicted chemical structure of the member alone. For example, a mass defect of reaction may be due to one or more water or other molecules that are, e.g., electrostatically associated with the library member. In addition, library members that experienced conditions that should have produced a common chemical transformation and change in molecular weight for all compounds in the group (i.e., library members with a shared chemical history), may have identical, different, or no mass defects of reaction.

The phrase "structural identification" refers to the identification of all, or a constituent part (e.g., a substituent or functional group) of a compound's chemical or physical structure.

A "fingerprint" refers to a representation of a compound or library that describes a set of attributes (descriptors), such as atom connectives, 3-D structure or physical properties. For example, the representation can be a numerical representation, an image (e.g., a barcode), or the like. See, e.g., Pickett et al. (1998) "Strategies for the design and comparison of combinatorial libraries using pharmacophoric descriptors," *J. Chem. Inf. Comput. Sci.* 38:144–150 and McGregor and Muskal (1999) "Pharmocophore fingerprinting 1. application to QSAR and focused library design," *J. Chem. Inf. Comput. Sci.* 39:569–574. A "descriptor" refers to a numerical representation of a molecular property, including, e.g., bulk properties (e.g., log P, molecular weight or mass), two-dimensional (2-D) features (atom connectivities) or three-dimensional (3-D) features (molecular shape). A fingerprint comprises a set of descriptors.

DETAILED DISCUSSION OF THE INVENTION

Introduction

Combinatorial chemistry is used to produce large numbers of related compounds. Typically, combinatorial synthesis is conducted via multi-step synthesis that includes the use of different building blocks to form different compounds, the use of different organic or inorganic reagents which alter where the building blocks are added, resulting in the generation of collections of related compounds, commonly referred to by those skilled in the art as "libraries." Synthetic chemical libraries produced by combinatorial synthesis are important tools for pharmaceutical lead discovery, compound optimization, and many other purposes. The different technologies and strategies used in the production of combinatorial libraries are well developed. Many of the techniques devised to prepare libraries on solid supports exploit the efficient "split-and-pool" or "split/pool" method to assemble all possible combinations of a set of building blocks. The split/pool method utilizes a pool of solid supports (e.g., particles of resin or the like) containing reactive chemical moieties that are initially spilt such that all particles in each split pool are subject to a different first reaction or randomization, resulting in different chemical modifications to each of the pools. After reaction the pools of solid supports are combined, mixed and split again into a second group of pools. Each split pool is subject to a second reaction or randomization which is different for each of the pools. The process is continued until a library of target compounds is formed. Following synthesis, library members are typically analyzed to identify structure, e.g., to assure synthetic quality.

For purposes of clarity, the methods described herein are discussed primarily with regard to identifying structure based on mass measurements, mass changes, and the like. However, it will be understood by those of skill in the art that essentially any other distinguishing physical property (e.g., chromatographic retention times, emission spectra, absorption spectra, or the like), or combinations of such properties (e.g., a fingerprint), can also be used to identify members of combinatorial libraries according to the methods provided by the present invention. Many of these properties (and devices for their detection) are referred to herein or are otherwise widely known in the art.

In overview, the present invention includes methods for the analysis of, e.g., mass spectrometry data in which information regarding a compound is derived from the compound data as well as data obtained from related compounds. The analysis is accomplished by using partial or complete information about molecular weights of compounds before transformation and partial or complete information about molecular weights of compounds after transformation. There is typically a common difference in molecular weights before and after the transformation for the majority of compounds undergoing a chemical, physical, or biological transformation (i.e., amongst those with a SCH). An objective of the methods is to determine unknown values prior to the analysis of the difference in molecular weights or to select this difference from a set of fixed values and to find the relationship between compounds before and after, e.g., chemical transformation. One embodiment is based on the sequential logical exclusion of variants not including an identical difference in molecular weight of a set of compounds before and after transformation. Other embodiments are based on the statistical analysis of compounds with an identical difference in the molecular weight of a set of compounds before and after, e.g., chemical transformation. Another embodiment is based on the solution of a system of equations describing the alteration of molecular weights as a result of, e.g., chemical transformation. Further, the invention includes methods for the selection of compounds originating from chemical reactions where one of the reactants is common with the same difference in molecular weights before and after reaction.

One application of the methods and related systems of the invention is in the analysis of the products of combinatorial synthesis. An unexpected result of these methods of analysis is a significant increase in the information content of mass measurement data, with the result that structures can unambiguously be determined based on a small number of mass measurements. In particular, the invention provides for selecting from a set of $\Delta M$ a value which best fits the case where some or all of the values in the initial and final sets of MW originate from compounds with a shared chemical history. The invention also provides for determining unexpected values of $\Delta mw$ assuming that all or some of the values in the initial and final sets of MW originate from compounds with a shared chemical history and for the validation of the hypothesis that all values in the initial and final sets of MW may be described as originating from or relating to compounds with a shared chemical history. In addition, the invention relates to the selection of values out of initial or final sets of MW which may not be described as being obtained from or related to compounds with a shared chemical history, and for the selection of subsets of values out of initial and final sets of MW which may be described as being obtained from or related to compounds with a shared chemical history. These and other features of the invention will be apparent upon a complete review of this disclosure.

Structural Identification Methods

The present invention includes a method of identifying predicted or actual structures of two or more members of a chemical or physical library. In preferred embodiments, the method is completely or partially computer implemented. Systems for performing the methods described herein are described below. The method generally includes (a) providing a logical matrix such as a data table which includes virtual masses of members of a complex library (e.g., a combinatorial chemical library) produced by chemical or physical transformations of an initial set of chemical or physical members in which at least one group of the virtual masses includes complex library members having a shared chemical history. Table 1, which is described further below, illustrates one example of a logical matrix utilized in the methods described herein. Optionally, multiple groups of the virtual masses include complex library members having shared chemical histories.

The method also includes (b) correlating molecular mass measurements (e.g., mass spectrometric measurements) of two or more chemical or physical library members having a shared chemical history with two or more virtual masses in the logical matrix to identify one or more groups of virtual masses that most likely describe chemical or physical transformations undergone by the two or more chemical or physical library members. In certain embodiments, the one or more groups of virtual masses describe the chemical or physical transformations undergone by the two or more chemical or physical library members in (b). Additionally, the correlations in (b) generally account for one or more mass defects of reaction. Finally, the method includes (c) identifying the predicted or actual structures of the two or more chemical or physical library members within the one or more identified groups based on the molecular mass measurements.

Individual masses of the initial set of chemical or physical members are optionally known or unknown. The mass of each member of the initial set of chemical or physical members is optionally determined using a mass spectrometer. In certain embodiments, the chemical or physical transformations include multiple chemical or physical transformations to the initial set of chemical or physical members. For example, the chemical or physical transformations optionally include additions of one or more common scaffolds to each of the initial set of chemical or physical members. Furthermore, the two or more chemical or physical library members are typically members of a synthesized set of compounds. For example, the method optionally further includes synthesizing the two or more chemical or physical library members, which library members correspond to all or a portion of the virtual masses represented in the logical matrix. The synthesized libraries of the present invention typically include library sizes in the range of between about two and about $10^9$ members, more typically in the range of between about 50 and about $10^8$ members, and usually in the range of between about 100 and about $10^7$ members. Combinatorial synthetic methods appropriate for use with the structural identification methods of the present invention are described in greater detail below.

FIG. 1 schematically further illustrates certain general steps of the methods described herein that are optionally computer implemented, e.g., by system software of the systems described herein. As shown, in A1 the method includes correlating mass measurements of two or more library members having a shared chemical history with two or more virtual masses in the logical matrix (e.g., two or more entries in a data table of predicted or actual masses corresponding to two or more library members) to identify one or more groups of virtual masses that most likely describe transformations undergone by the two or more library members. In A2, the method includes identifying the structures of the two or more chemical or physical library members within the one or more identified groups based on the mass measurements. These steps are typically effected under the direction of system software, which is discussed further below.

The present invention also includes methods of determining predicted or actual structures of two or more members of a chemical or physical library that include (a) providing a logical matrix including virtual masses of members of a complex library produced by chemical or physical transformations of an initial set of chemical or physical members in which one or more groups of the virtual masses include complex library members having a shared chemical history. This method also includes (b) providing at least one set of chemical or physical library members corresponding to two or more members of the complex library in which the at least one set of chemical or physical library members includes unknown structures or is non-arrayed. Finally, the method includes (c) correlating mass measurements of two or more of the chemical or physical library members to two or more virtual masses in one of the one or more groups to determine the predicted or actual structures of the two or more chemical or physical library members. The set of chemical or physical library members is typically provided using a combinatorial synthetic technique, such as any of those described herein.

Structural Identification by Sequential Logical Exclusion

In one aspect of the invention, the method includes the sequential logical exclusion of variants not including an identical difference in molecular weight of a set of compounds before and after transformation to identify structure. In this embodiment, (a) includes calculating individual masses for each member of the logical matrix by separately summing masses for each member of the initial set of chemical or physical members with each mass in a set of expected mass changes. Each calculated individual mass is assigned to one of m groups, m corresponding to a total number of individual mass changes in the set of expected mass changes. Furthermore, each of the m groups includes n members, n corresponding to a total number of members in the initial set of chemical or physical members.

In addition, (b) includes (i) matching a selected mass from the set of chemical or physical library members with all identical calculated masses and excluding any of the m groups lacking a member n comprising a mass identical to the selected mass from further consideration to reduce a number of m groups available for subsequent consideration. Thereafter, the method typically includes (ii) repeating (i) at least once, in which each repeated (i) includes matching a different selected mass from the set of chemical or physical library members with all the identical calculated masses that remain in the reduced number of m groups from an immediately preceding (i) and excluding any of the reduced number of m groups lacking an n member with a mass identical to the different selected mass from further consideration to further reduce the number of m groups available for subsequent consideration. This method leads to (1) identifying a single m group which indicates that matched masses from the set of chemical or physical library members have a shared chemical history, (2) identifying more than one m group for further consideration which indicates that insufficient data exists for an unambiguous determination of whether masses selected from the set of chemical or physical library members have a shared chemical history, or (3) identifying no m group for further consideration which indicates that masses selected from the set of chemical or physical library members originate from materials lacking a shared chemical history.

FIG. 2 schematically further illustrates the steps involved in this embodiment of the invention. As shown, the method includes A1, calculating matrix entries (ME) by separately summing masses for each member a of an initial set $\{a\}$ with each mass change $\Delta M$ in a set of expected mass changes $\{\Delta M_{exp}\}$ Following A1, the method includes A2, assigning each ME to one of m groups, where m corresponds to a total number $\Delta Ms$ in $\{\Delta M_{exp}\}$, and in which each m group includes n members, where n corresponds to a total number of as in $\{a\}$ and A3, matching a selected b mass from $\{b\}$ with all identical ME and excluding any of the m groups lacking a member n with a mass identical the selected b mass from further consideration to reduce the number of m groups available for subsequent consideration. Thereafter, the method includes A4, repeating A3 at least once, in which each repeated A3 includes matching a different selected b mass from $\{b\}$ with all the identical ME that remain in the reduced number of m groups from an immediately preceding A3 and excluding any of the reduced number of m groups lacking an n member with a mass identical to the different selected b mass from further consideration to further reduce the number of m groups available for subsequent consideration. As shown, the method leads to the results shown A5, namely, identifying an m group which indicates that matched selected b masses from $\{b\}$ have a shared chemical history, identifying more than one m group for further consideration which indicates that insufficient data exists for an unambiguous determination of whether selected b masses from $\{b\}$ have a shared chemical history, or identifying no m group for further consideration which indicates that selected b masses from $\{b\}$ originate from materials lacking a shared chemical history. As with all of the methods described herein, these steps are typically effected under the direction of system software, which is discussed further below.

This embodiment of the invention is typically applied to cases when all values in a final set of MW are assumed to originate from or be related to compounds with a shared chemical history, and for which a set of expected $\Delta mw$ is known. The method is intended to select a value in a set of expected $\Delta mw$ which fits the data in a final set of MW and finds all paired values in the initial and final sets of MW which may be described as originating from compounds with a shared chemical history. An advantage of this embodiment is that, generally, only a small sub-set of values from the final set of MW is utilized for an unambiguous selection of a unique $\Delta mw$ out of a set of expected $\Delta mw$ values. Of course, if values selected from the final set of MW do not originate from compounds with a shared chemical history, the correct $\Delta mw$ will not be selected out of the set of expected $\Delta MWs$. This embodiment is illustrated further in Example 1, below.

Statistics-based Structural Identification

Certain embodiments of the structural identification methods described herein are based on a statistical analysis of compounds that is intended to select values in a set of expected mass changes that best fit the data in a set of chemical or physical library members and to find all paired values in the initial and final sets of MW that may be described as originating from compounds with a shared chemical history. In these embodiments, (a) includes calculating individual masses for each member of the logical matrix by separately summing masses for each member of the initial set of chemical or physical members with each mass in a set of expected mass changes. Optionally, the set of expected mass changes includes a set of virtual mass changes calculated by separately subtracting masses for each member of the initial set of chemical or physical members from each mass in the set of chemical or physical library members. Each calculated individual mass is assigned to one of m groups, m corresponding to a total number of individual mass changes in the set of expected mass changes. Furthermore, each of the m groups includes n members, n corresponding to a total number of members in the initial set of chemical or physical members.

In these embodiments, the method further includes assigning each of the m groups a P variable in which each P variable is typically initially zero. Optionally, each P variable is initially set at some other arbitrary initial value, e.g., that is common to each m group. An additional option includes weighting particular m groups, e.g., by setting P variables for those groups at different initial values (e.g., higher or lower) than for other m groups. In these embodiments, (b) includes (i) matching a selected mass from the set of chemical or physical library members with identical masses in each of the m groups in which the P variable for an m group is increased by one when the selected mass matches at least one value therein. Thereafter, these embodiments include (ii) repeating (i) for each remaining value in the set of chemical or physical library members, and (iii) determining which one or more m groups have highest P variables to identify one or more mass changes from the set of expected mass changes best fitting the set of chemical or physical library members. It also identifies all paired values in the initial set of chemical or physical members and the set of chemical or physical library members originating from materials with a shared chemical history.

FIG. 3 schematically further illustrates the steps involved in this embodiment of the invention. As shown, A1 includes calculating matrix entries (ME) by separately summing masses for each member a of an initial set {a} with each mass change ΔM in a set of expected mass changes {ΔM$_{exp}$}. In A2, the method includes; assigning each ME to one of m groups, where m corresponds to a total number ΔMs in {ΔM$_{exp}$}, and in which each m group includes n members, where n corresponds to a total number of a in {a} and A3 includes assigning each of the m groups a P variable in which each P is typically initially zero. Thereafter, the method (in A4) includes matching a selected b mass from {b} with identical ME in each of the m groups in which the P for an m group is increased by one when a match occurs and A5 repeating A4 for each remaining b mass from {b}. As shown in A6, the method leads to determining which one or more m groups have highest Ps to identify one or more ΔMs in {ΔM$_{exp}$} best fitting {b}, and all paired values in {a} and {b} with a shared chemical history. As with all of the methods described herein, these steps are typically effected under the direction of system software (e.g., as part of a combinatorial synthesis and structural identification system) which is discussed further below.

This embodiment may be applied, e.g., to cases when most but not necessarily all values in the final set of MW are assumed to originate from or be related to, compounds with a shared chemical history, and for which a set of expected Δmw is known. As mentioned, the method is intended to select values in a set of expected Δmw which best fit the data in the final set of MW and to find all paired values in the initial and final sets of MW which may be described as originating from compounds with a shared chemical history. The difference from the method involving the sequential logical exclusion of variants (described above) is that a group is not eliminated from consideration if it does not contain matching data. Instead, each m group accumulates a value or score (P variable) depending on how many values from a final set of MW match at least one value in the particular m group. Thus, the P variable for each of m group of calculated molecular weights equals the number of values in the final set of MW that match values expected in this group. For example, if as a result of processing data from group m by this method there is a group with a score that equals the number of values in the final set of MW, all values in the final set originate from compounds with a shared chemical history. An advantage of this method is that even if some of the values in the final set of MW do not originate from compounds with a shared chemical history, the Δmw that fits most of the data in the final set of MW can be unambiguously determined based on the group with the highest P values.

As indicated above, the set of expected mass changes optionally includes a set of virtual mass changes calculated by separately subtracting masses for each member of the initial set of chemical or physical members from each mass in the set of chemical or physical library members. This aspect of the invention may be applied, e.g., to cases when most but not necessarily all values in the final set of MW are assumed to originate from, or be related to, compounds with a shared chemical history, and for which a set of expected Δmw is unknown. This aspect of the method is intended to determine a value of Δmw which fits the best data in the final sets of MW and to find all paired values in the initial and final sets of MW that may be described as originating from compounds with a shared chemical history. Examples illustrating these embodiments are provided below.

Simultaneous System of Equations

The invention also provides embodiments of the methods described herein that are based on the algebraic solution of a system of equations that does not require a set of expected Δmw to be known. These embodiments may be applied, e.g., to cases where: (a) the number of values in the final set of MW equals the number of values in an initial set of MW and all values may be described as originating from compounds with a shared chemical history, or (b) a number of values in the final set of MW is or is not equal the number of values in the initial set of MW and all or less than all values may be described as originating from compounds with a shared chemical history.

Essentially any value in a final set of MW of compounds with a shared chemical history can be described by the linear equation: a+Δmw=b. Since prior to analysis it is not known which of the values in an initial set of MW corresponds to which values in the final set of MW, the equation has to be modified (i.e., split) into a system of equations, as follows:

$$x_1 + \Delta mw = b_1$$

$$x_2 + \Delta mw = b_2$$

$$\ldots$$

$$x_n + \Delta mw = b_n, \text{ where}$$

Δmw is unknown or belongs to the set of expected Δmws, and $x_1, x_2, \ldots x_n$ belong to the initial set of MW. The latter condition allows one more equation, namely, $x_1+x_2+\ldots+x_n=a_1+a_2+\ldots+a_n$, to be added to the system, thereby making it solvable with a unique solution. That is, the system of equations can be solved using standard linear algebraic approaches. See, e.g., Grossman, *Elementary Linear Algebra*, 3$^{rd}$ Ed., Wadsworth Publishing Company, Belmont, Calif. (1987). Thus, if the number of values in the initial and final sets of MW is equal and all data are described as originating from compounds with a shared chemical history, then the Δmw may be determined unambiguously and all pairs of values in the initial and final sets of MW are identified. It is important to note that if the assumption that all data may be described as originating from compounds with a shared chemical history is not true, the system of equations described above will have a unique solution which will not fit the data.

If the number of values in the final set of MW is not equal to the number of values in the initial set of MW, then for an unambiguous solution of the system of equations described above, the number of variables cannot exceed the number of values in the smaller set of data. If some data may not be described as originating from compounds with a shared chemical history, then to obtain a result fitting most data, the data and equations associated with them have to be removed form the system of equations described above. Since a priori it is not known which data have to be removed from consideration, all possible systems of equations with the smaller number of variables must be solved and checked for fitting the data. All systems of equations providing solutions fitting the initial and final sets of MW will relate to subsets of data, which may be described as originating from compounds with a shared chemical history.

As a result, in certain embodiments of the methods described herein, (a) includes solving a simultaneous system of equations to provide one or more values in the logical matrix. For example, solving the simultaneous system of equations optionally includes solving for one or more masses of one or more members of the initial set of chemical or physical members. Optionally, solving the simultaneous system of equations includes solving for one or more of: at least one mass of at least one member of the set of chemical or physical library members, at least one mass of at least one of the initial set of chemical or physical members, or at least one member of a set of expected mass changes.

In one aspect of these embodiments, (b) includes (i) determining the molecular mass measurements for each of x members of a set of chemical or physical library members, wherein x is at least two, and wherein each x member is derived from one member of the initial set of chemical or physical members and comprises a shared chemical history with all other x members. This embodiment also includes (ii) subtracting a cumulative total mass of all members of the initial set of chemical or physical members from a cumulative total mass of all x members of the set of chemical or physical library members to determine a cumulative total mass change for the set of chemical or physical library members and (iii) dividing the cumulative total mass change by x to thereby determine a mass change for each of the x members of the set of chemical or physical library members. In addition, this embodiment includes (iv) subtracting the mass change of (iii) from each of the molecular mass measurements of (i) to thereby identify each member in the initial set of chemical or physical members corresponding to each individual x member of the set of chemical or physical library members.

FIG. 4 schematically further shows steps involved in solving a system of equations to identify members of an initial of chemical or physical members corresponding to members in a set of chemical or physical library members. As shown, step A1 includes determining masses for each x member of a synthesized library $\{b_x\}$ in which each b is derived from a member a of an initial set $\{a\}$ and has a shared chemical history with all other members of $\{b_x\}$ Step A2 includes subtracting a total mass of $\{a\}$ from a total mass of $\{b_x\}$ to determine a total mass change $\Delta M_{tot}$ of $\{b_x\}$ and step A3 includes dividing $\Delta M_{tot}$ by x to determine a mass change $\Delta M_x$ for each b of $\{b_x\}$. Finally, step A4 includes subtracting $\Delta M_x$ from each b of $\{b_x\}$ to identify each a of $\{a\}$ corresponding to each b. An example illustrating the use of a system of equations is provided below.

Shared Initial Mass Determinations

In one alternative embodiment, the present invention provides a method of determining predicted or actual structures for one or more members of a chemical or physical library that includes (a) providing a physical or logical matrix corresponding to masses for a set of members of a complex library produced by chemical or physical transformations of an initial set of chemical or physical members. The method also includes (b) correlating at least one mass measurement of at least one set of chemical or physical library members corresponding to one or more members of the complex library to the physical or logical matrix to determine the structure of the one or more chemical or physical library members. Certain aspects of this method further include determining whether the one or more chemical or physical library members have a shared initial mass. In these embodiments, (a) includes calculating individual masses for each member of the physical or logical matrix by separately summing masses for each of the initial set of chemical or physical members with each mass in a set of expected mass changes. Optionally, the set of expected mass changes includes a set of virtual mass changes that is calculated by separately subtracting masses for each of the initial set of chemical or physical members from each mass in the set of chemical or physical library members corresponding to the complex library. Each calculated individual mass is assigned to one of n groups, n corresponding to a total number of individual masses in the initial set of chemical or physical members, and wherein each of the n groups comprises m members, m corresponding to a total number of individual mass changes in the set of expected mass changes.

In these embodiments, (b) optionally includes (i) matching a selected mass from the set of chemical or physical library members corresponding to the complex library with all identical calculated masses and excluding any of the n groups lacking a member m comprising a mass identical to the selected mass from further consideration to thereby reduce a number of n groups available for subsequent consideration. This embodiment also includes (ii) repeating (i) at least once in which each repeated (i) includes matching a different selected mass from the set of chemical or physical library members corresponding to the complex library with all the identical calculated masses that remain in the reduced number of n groups from an immediately preceding (i) and excluding any of the reduced number of n groups lacking an m member with a mass identical to the different selected mass from further consideration to further reduce the number of n groups available for subsequent consideration. This method leads to (1) identifying a single n group which indicates that matched masses from the set of chemical or physical library members corresponding to the complex library have a shared initial mass, (2) identifying more than one n group for further consideration which indicates that insufficient data exists for an unambiguous determination of whether masses selected from the set of chemical or physical library members corresponding to the complex library have a shared initial mass, or (3) identifying no n group for further consideration which indicates that masses selected from the set of chemical or physical library members corresponding to the complex library originate from materials lacking a shared initial mass.

FIG. 5 schematically further shows steps involved in this embodiment of the invention for determining whether selected members from a final set of library members have a shared initial mass. As shown, A1 includes calculating matrix entries (ME) by separately summing masses for each member a of an initial set $\{a\}$ with each mass change $\Delta M$ in a set of expected mass changes $\{\Delta M_{exp}\}$ and A2 assigning each ME to one of n groups, where n corresponds to a total number of a in $\{a\}$ and in which each n group includes m members, where m corresponds to a total number $\Delta Ms$ in $\{\Delta M_{exp}\}$ Thereafter, A3 includes matching a selected b mass from $\{b\}$ with all identical ME and exclude any of the n groups lacking a member m with a mass identical the selected b mass from further consideration to reduce the number of n groups available for subsequent consideration, and A4 repeating A3 at least once, in which each repeated A3 includes matching a different selected b mass from $\{b\}$ with all the identical ME that remain in the reduced number of n groups from an immediately preceding A3 and excluding any of the reduced number of n groups lacking an m member with a mass identical to the different selected b mass from further consideration to further reduce the number of n groups available for subsequent consideration. As shown in A5, this leads to three outcomes, namely, identifying a single n group which indicates that matched selected b masses from $\{b\}$ have a shared initial mass, identifying more than one n group for further consideration which indicates that insufficient data exists for an unambiguous determination of whether selected b masses from $\{b\}$ have a shared initial mass, or identifying no n group for further consideration which indicates that selected b masses from {b} originate from materials lacking a shared initial mass. As with all of the methods described herein, these steps are typically effected under the direction of system software, which is discussed further below.

In certain embodiments, these methods further include assigning each of the n groups a Q variable in which each Q variable is typically initially zero. Optionally, each Q variable is initially set at some other arbitrary initial value, e.g., that is common to each n group. An additional option includes weighting particular n groups, e.g., by setting Q variables for those groups at different initial values (e.g., higher or lower) than for other n groups. In these embodiments, (b) includes (i) matching a selected mass from the set of chemical or physical library members corresponding to the complex library with identical masses in each of the n groups in which the Q variable for an n group is increased by one when the selected mass matches at least one value therein, and (ii) repeating (i) for each remaining value in the set of chemical or physical library members corresponding to the complex library. The method also includes (iii) determining which one or more n groups have highest variable Qs, thereby identifying one or more initial masses from the initial set of chemical or physical members best fitting the set of chemical or physical library members corresponding to the complex library, and all paired values in the initial set of chemical or physical members and the set of chemical or physical library members corresponding to the complex library originating from materials with a shared initial mass.

FIG. 6 schematically further shows steps involved in this embodiment of the structural identification method that utilizes Q variables. As shown, A1 includes calculating matrix entries (ME) by separately summing masses for each member a of an initial set {a} with each mass change $\Delta M$ in a set of expected mass changes $\{\Delta M_{exp}\}$, A2 includes assigning each ME to one of n groups, where n corresponds to a total number of a in {a} and in which each n group includes m members, where m corresponds to a total number $\Delta$Ms in $\{\Delta M_{exp}\}$ and A3 includes assigning each of the n groups a Q variable in which each Q is typically initially zero. Thereafter, A4 includes matching a selected b mass from {b} with identical ME in each of the n groups in which the Q for an n group is increased by one when a match occurs, and A5 includes repeating A4 for each remaining b mass from {b}. As shown in A6, the method leads to determining which one or more n groups have highest Qs to identify one or more masses a from {a} best fitting {b}, and all paired values in {a} and {b} with a shared initial mass. As with all of the methods described herein, these steps are typically effected under the direction of system software, which is discussed further below.

Structural Identification and Synthesis Systems

The present invention also provides a system for identifying predicted or actual structures for two or more members of a chemical or physical library. The system includes a computer (e.g., an information appliance, digital device, P.C., or the like) that includes a database having a logical matrix that includes virtual masses of members of a complex library produced by chemical or physical transformations of an initial set of chemical or physical members in which at least one group of the virtual masses includes complex library members having a shared chemical history. The system also includes system software that includes one or more logic instructions for (i) correlating molecular mass measurements of two or more chemical or physical library members having a shared chemical history with two or more virtual masses in the logical matrix to identify one or more groups of virtual masses that most likely describe chemical or physical transformations undergone by the two or more chemical or physical library members. The correlations in (i) generally account for one or more mass defects of reaction. The system software also includes one or more logic instructions for (ii) identifying the predicted or actual structures of the two or more chemical or physical library members within the one or more identified groups based one the molecular mass measurements. In some embodiments, the one or more groups of virtual masses describe the chemical or physical transformations undergone by the two or more chemical or physical library members in (b). The system software is generally stored on, e.g., a CD-ROM, a floppy disk, a tape, a flash memory device or component, a system memory device or component, a hard drive, a data signal embodied in a carrier wave, or the like.

The system also generally includes components for the synthesis of combinatorial libraries (e.g., a set of chemical or physical library members). For example, the system typically includes a plurality of reaction vessels (e.g., flasks, test tubes, wells of one or more microwell plates, or the like), a handling system (including, e.g., a solid support handler, such as a bead handler, a bead container handler, or the like) configured to translocate solid phase synthesis units (e.g., individual beads, tea-bags, or other containers having multiple beads or other solid supports disposed therein) and/or reagents to and from the plurality of reaction vessels, and a detection system, which is generally a mass spectrometer, to detect masses of combinatorial library members for correlation with virtual masses in the logical matrix according to any of the methods described herein. The system software typically further directs the operation of the handling and detection systems which are both generally operably connected to the computer. Combinatorial synthesis methods optionally performed with the systems of the invention are described in greater detail below. Further details regarding these synthesis methods are also found in co-filed application "Nonredundant Split/Pool Synthesis of Combinatorial Libraries" by Sepetov et al., U.S. Ser. No. 09/776,233.

Additional details relating to the automation of combinatorial synthetic and structural identification methods are described in, e.g., Cargill and Maiefski (1996) "Automated combinatorial chemistry on solid phase," *Lab. Robotics. Automation* 8:139–148, Zuckermann et al. (1992) "Design, construction and application of a fully automated equimolar peptide mixture synthesizer," *Int. J. Peptide Prot. Res.* 40:497–506, Castelino et al. (2000) "Automated sample storage for drug discovery," *Chim. Oggi.* 17:32–35, Davis and Swayze (2000) "Automated solid-phase synthesis of linear nitrogen-linked compounds," *Biotechnol. Bioeng.* 71:19–27, Groger et al. (2000) "1,3,5-Triazines, versatile industrial building blocks: Synthetic approaches and applications," *Chim. Oggi.* 18:12–16, Haag (2000) "Chemspeed Ltd.: Automated and unattended parallel synthesis integrating work-up and analysis," *Chimia* 54:163–164, Hu et al. (2000) "Automated solid-phase synthesis and photophysical properties of oligodeoxynucleotides labeled at 5'-aminothymidine with Ru(bpy)(2)(4-m-4'-cam-bpy)(2+)," *Inorg. Chem.* 39:2500–2504, Lewis et al. (2000) "Automated high-throughput quantification of combinatorial arrays," *American Pharmaceutical Review* 3:63–68, North (2000) "Implementation of analytical technologies in a pharmaceutical development organization-looking into the next millennium," *Journal of Automated Methods and Management in Chemistry* 22:41–45, and Keifer et al. (2000)

"Direct-injection NMR (DI-NMR): A flow NMR technique for the analysis of combinatorial chemistry libraries," *Journal of Combinatorial Chemistry* 2; 151–171.

Controllers

The handling systems of the invention typically incorporate one or more controllers, either as separate or integral components, which are generally utilized, e.g., to regulate the quantities of reagents dispensed and the segregation and distribution of solid phase synthesis units. A variety of available robotic elements (robotic arms, movable platforms, etc.) can be used or modified for these purposes.

For example, controllers typically direct dipping of bead handling elements of the handling systems into, e.g., selected wells on microwell plates, or other reaction vessels, to dispense or extract, e.g., selected beads or other solid phase synthesis units. Typically, the controller systems of the present invention are appropriately configured to receive or interface with a reaction vessel or system element as described herein. For example, the controller and/or detector, optionally includes a stage upon which the reaction vessels of the invention are disposed or mounted to facilitate appropriate interfacing among, e.g., a bead handler and/or detector and a particular reaction vessel. Typically, the stage includes an appropriate mounting/alignment structural element, such as alignment pins and/or holes, a nesting well, or the like to, e.g., facilitate proper device alignment.

Figure 7B:
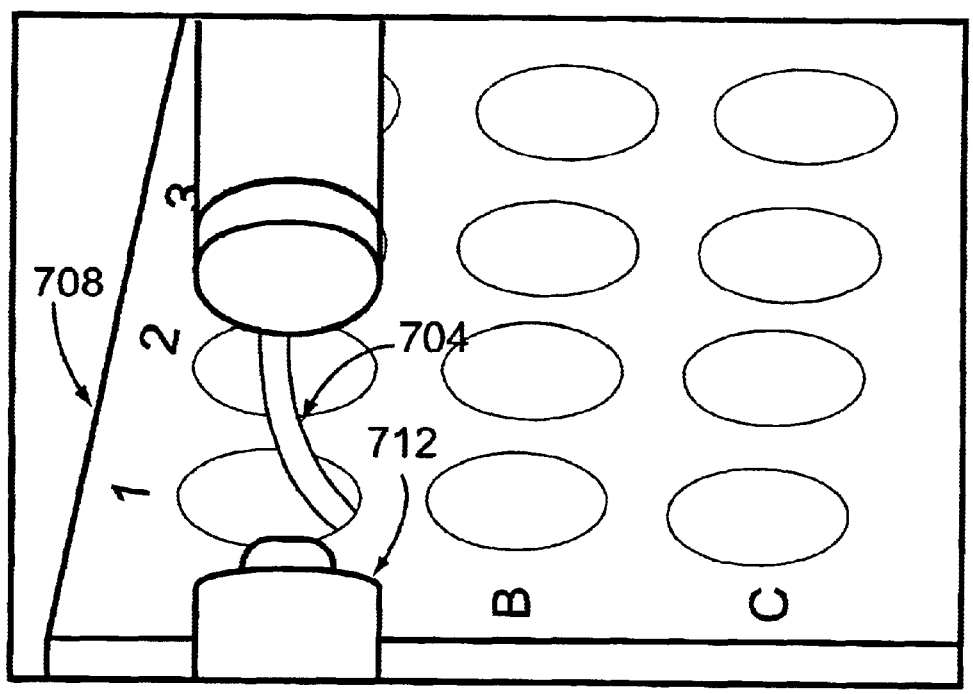
FIG. 7B schematically shows a bead handler of one embodiment of a handling system distributing single beads to a well of a microwell plate.

FIG. 7A schematically depicts aspects of one example of a bead handling system. As shown, handling system 700 includes robotic armature 702. The handling system is depicted with bead handler 704 hunting for beads in pooling vessel 706 for distribution to the wells of microwell plate 708. Robotic armature 702 is operably connected via connection 710 to at least one controller (not shown). Detector 712 is also included in this embodiment. As also shown, pooling vessel 706 and microwell plate 708 are disposed on stage 714. FIG. 7B schematically illustrates a magnified view of bead handler 704 distributing beads to a well of microwell plate 708. Detector 712 is also depicted.

Detector

In preferred embodiments, mass is the distinguishing physical property utilized, e.g., to identify the structure of a selected synthesis product as described herein. mass is detected via mass spectrometric methods. Mass spectrometry is a widely used analytical technique that is typically used to provide information about, e.g., the isotopic ratios of atoms in samples, the structures of various molecules, including biologically important molecules (e.g., transporter molecules, transmitters, enzymes, receptors, chemotactic factors, and the like), and the qualitative and quantitative composition of complex mixtures. Common mass spectrometer systems include a system inlet, an ion source, a mass analyzer, and a detector which are under vacuum. The detector is typically operably connected to a signal processor and a computer. Desorption ion sources for use in the present invention, include field desorption (FD), electrospray ionization (ESI), chemical ionization, matrix-assisted desorption/ionization (MALDI), plasma desorption (PD), fast atom bombardment (FAB), secondary ion mass spectrometry (SIMS), and thermospray ionization (TS).

Mass spectrometry is well-known in the art. In particular, mass spectrometry techniques for solid-phase synthesis are described in, e.g., Enjalbal et al., (2000) "Mass spectrometry in combinatorial chemistry," *Mass Spectrom. Rev.* 19:139–161, Lake et al. (2000) "Sample preparation for high throughput accurate mass analysis by matrix-assisted laser desorption/ionization time-of-flight mass spectrometry," Rapid *Commun. Mass Spectrom.* 14:1008–1013, Brummel et al. (1996) "Evaluation of Mass Spectrometric Methods Applicable to the Direct Analysis of Non-Peptide Bead-Bound Combinatorial Libraries," *N. Anal. Chem.* 68:237–242, Hughes (1998) "Design of self-coded combinatorial libraries to facilitate direct analysis of ligands by mass spectrometry," *Med. Chem.* 41:3804–3811, Carrasco et al. (1997) "Direct Monitoring of Organic Reactions on Polymeric Supports," *Tetrahedron Lett.* 38:6331–6334, Berlin et al. (1997) "Spectrometrically Monitored Selection Experiments-Quantitative Laser Desorption Mass Spectrometry of Small Chemical Libraries," *Chem. Biol.* 4:63–77, Newcomb et al. (1998) "Analysis of 9-fluorenylmethoxycarbonyl (Fmoc) loading of solid-phase synthesis resins by gas chromatography," *Biotech. Bioeng.* (Comb. Chem.) 61:55–60, Demirev and Zubarev (1997) "Probing combinatorial library diversity by mass spectrometry," *Anal. Chem.* 69:2893–2900, Haap et al. (1998) "FT-IR Mapping—A New Tool for Spatially-Resolved Characterization of Polymer-Bound Combinatorial Compound Libraries with Ir Microscopy," *Angew. Chem. Int. Ed.* 37(23):3311–3314, Schriemer et al. (1998) "Microscale Frontal Affinity-Chromatography with Mass-Spectrometric Detection—A New Method for the Screening of Compound Libraries," *Angew. Chem. Int. Ed.* 37(24):3383–3387, and van Breemen et al. (1997) "Pulsed ultra-filtration mass spectrometry: A new method for screening combinatorial libraries," *Anal. Chem.* 69:2159–2164. General sources of information about mass spectrometry include, e.g., Skoog, et al. *Principles of Instrumental Analysis* (5$^{th}$ Ed.) Hardcourt Brace & Company, Orlando (1998).

The systems of the present invention optionally include various other signal detectors, e.g., which detect concentration, fluorescence, phosphorescence, radioactivity, pH, charge, absorbance, refractive index, luminescence, temperature, magnetism, or the like. As mentioned, while the discussion herein focuses masses, mass changes, or the like, any other detectable distinguishing properties are optionally utilized to identify or otherwise characterize combinatorial library members according to the methods described herein. The detector(s) optionally monitors one or a plurality of signals from upstream and/or downstream of the performance of a given synthesis step. For example, the detector optionally monitors a plurality of optical signals, which correspond in position to "real time" results. Example detectors or sensors include photomultiplier tubes, CCD arrays, optical sensors, temperature sensors, pressure sensors, pH sensors, conductivity sensors, scanning detectors, or the like. The detector optionally moves relative to assay components, or alternatively, assay components, such as samples of selected synthesis products move relative to the detector. Optionally, the systems of the present invention include multiple detectors. Each of these types of sensors is optionally readily incorporated into the systems described herein. In these systems, such detectors are typically placed either in or adjacent to, e.g., a particular reaction vessel, such that the detector is within sensory communication with the reaction vessel. The phrase "within sensory communication" of a particular region or element, as used herein, generally refers to the placement of the detector in a position such that the detector is capable of detecting the property of the reaction vessel or portion thereof, the contents of a portion of the vessel, or the like, for which that detector was intended. The detector optionally includes or is operably linked to a computer, e.g., which has system software for converting detector signal information into assay result information or the like.

The detector optionally exists as a separate unit, or is integrated with the handling or controller system, into a single instrument. Integration of these functions into a single unit facilitates connection of these instruments with the computer (described below), by permitting the use of few or a single communication port(s) for transmitting information between system components.

Specific detection systems that are optionally used in the present invention (e.g., in addition to, or in lieu of, a mass spectrometer) include, e.g., an emission spectroscope, a fluorescence spectroscope, a phosphorescence spectroscope, a luminescence spectroscope, a spectrophotometer, a photometer, a nuclear magnetic resonance spectrometer, an electron paramagnetic resonance spectrometer, an electron spin resonance spectroscope, a turbidimeter, a nephelometer, a Raman spectroscope, a refractometer, an interferometer, an x-ray diffraction analyzer, an electron diffraction analyzer, a polarimeter, an optical rotary dispersion analyzer, a circular dichroism spectrometer, a potentiometer, a chronopotentiometer, a coulometer, an amperometer, a conductometer, a gravimeter, a thermal gravimeter, a titrimeter, a differential scanning calorimeter, a radioactive activation analyzer, a radioactive isotopic dilution analyzer, or the like.

Computers

As noted above, the systems of the present invention typically include a computer (or other information appliance) operably connected to or included within various system components. As described herein, the computer typically includes system software that directs, e.g., the mass correlations of the structural identification methods of the invention. The system software also generally directs the handling and detection systems to, e.g., segregate or distribute solid phase synthesis units into selected reaction vessels, deliver various reagents (e.g., different components or building blocks, scaffolds, or the like) to selected reaction vessels, detect distinguishing physical properties of selected members of combinatorial libraries, or the like. Additionally, the handling/controller system and/or the detection system is/are optionally coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

Standard desktop applications such as word processing software (e.g., Microsoft Word™ or Corel WordPerfect™) and database software (e.g., spreadsheet software such as Microsoft Excel™, Corel Quattro PrO™, or database programs such as Microsoft Access™ or Paradox™) can be adapted to the present invention by inputting character strings corresponding to reagents or masses, or other distinguishing physical properties, thereof. For example, the systems optionally include the foregoing software having the appropriate character string information, e.g., used in conjunction with a user interface (e.g., a GUI in a standard operating system such as a Windows, Macintosh or LINUX system) to manipulate strings of characters, e.g., into data tables, e.g., in Microsoft Excel™ or a database program.

The computer can be, e.g., a PC (Intel x86 or Pentium chip-compatible DOS™, OS2™, WINDOWS™, WINDOWS NT™, WINDOWS95™, WINDOWS98™, LINUX based machine, a MACINTOSH™, Power PC, or a UNIX based (e.g., SUN™ work station) machine) or other commercially common computer which is known to one of skill. Software for performing the methods described herein is optionally easily constructed by one of skill using a standard programming language such as Visual basic, Fortran, Basic, Java, or the like. Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation, e.g., varying or selecting the rate or mode of movement of various system components, directing X-Y-Z translation of the bead handler, or of one or more microwell plates or other reaction vessels, or the like. The computer then receives the data from the one or more sensors/detectors included within the system, and interprets the data, either provides it in a user understood format, or uses that data to initiate further controller instructions, in accordance with the programming, e.g., such as in monitoring reaction temperatures or the like.

In addition, one approach for refining a system's ability to recognize patterns in data sets, or refine such pattern recognition is to use a heuristic learning approach, a neural network approach and/or a genetic algorithm to refine such models. By using such predictive system components, the systems gradually becomes more efficient at selecting "correct" masses, or, e.g., predicting whether any discrepancy between actual and predicted masses is constant, or observing any trends or principle data components, or the like. A variety of approaches can be used to manipulate or consider data in a system, including principle component analysis, use of positive or negative data, data parameterization, consideration of whether predictions meet observed phenomena use of genetic algorithms, neural networks or other heuristic learning components, etc.

For example, Partek Incorporated (St. Peters, Mo.; www.partek.com) provides software for pattern recognition (e.g., which provide Partek Pro 2000 Pattern Recognition Software) which can be applied to genetic algorithms for multivariate data analysis, interactive visualization, variable selection, neural & statistical modeling. Relationships can be analyzed, e.g., by Principal Components Analysis (PCA) mapped scatterplots and biplots, Multi-Dimensional Scaling (MDS) mapped scatterplots, Star plots, etc. Further information regarding genetic algorithms and neural networks can be found in David E. Goldberg (1989) *Genetic Algorithms in Search, Optimization and Machine Learning* Addison-Wesley Pub Co; ISBN: 0201157675; Timothy Masters (1993) *Practical Neural Network Recipes in C++* (Book&Disk edition) Academic Pr; ISBN: 0124790402; Kevin Gurney (1999) *An Introduction to Neural Networks*, UCL Press, 1 Gunpowder Square, London EC4A 3DE, UK; Christopher M. Bishop (1995) *Neural Networks for Pattern Recognition* Oxford Univ Press; ISBN: 0198538642; Brian D. Ripley, N. L. Hjort (Contributor) (1995) *Pattern Recognition and Neural Networks* Cambridge Univ Pr (Short);

ISBN: 0521460867 and in a variety of other currently available references. Additional details regarding computing systems of the present invention are described below.

Combinatorial Synthetic Methods

Essentially any synthesis method is optionally adapted for use with the methods of the present invention. For example, suitable solid phase synthesis methods are described in, e.g., Bunin et al. (1994) "The combinatorial synthesis and chemical and biological evaluation of 1,4-benzodiazepine library," *Proc. Natl. Acad. Sci. USA* 91:4708–4712, Bunin and Ellman (1992) "A general and expedient method for the solid phase synthesis of 1,4-benzodiazepine derivatives," *J. Amer. Chem. Soc.* 114:10997–10998, Meldal (1992) "PEGA: A flow stable polyethylene glycol dimethyl acryamide copolymer for solid phase synthesis," *Tetrahedron Lett.* 33:3077, and Merrifield (1985) "Solid phase synthesis (Nobel lecture)," *Angew. Chem.* 97:801. See, also, Seneci, *Solid Phase Synthesis and Combinatorial Technologies*, John Wiley & Sons, (2000), Burgess (Ed) *Solid-Phase Organic Synthesis*, John Wiley & Sons, (2000), and Kates and Albercio (Eds) *Solid-Phase Synthesis: A Practical Guide*, Marcel Dekker, (2000). In preferred embodiments, combinatorial synthesis is performed according to nonredundant split/pool methods. These synthetic methods are described below and in co-filed application "Nonredundant Split/Pool Synthesis of Combinatorial Libraries" by Sepetov et al., U.S. Ser. No. 09/776,233.

In brief, nonredundant split/pool synthesis methods generally include (a) providing at least n*m*f solid phase synthesis units in which n is equal to a number of choices of different first components in a first stage of synthesis, m is equal to a number of choices of different second components in a second stage of the synthesis, and f is equal to a number of solid phase synthesis units to include identical materials upon completion of the synthesis. In one class of embodiments, f is equal to one. Solid phase synthesis units are typically functionalized either by a linker for attaching reactants in the first randomization to the solid phase or by certain molecular structures which may be considered as the first point of diversity for combinatorial compounds. Optionally, one or more of the solid phase synthesis units include single functionalized particles or single non-functionalized particles (e.g., a controls or the like). As a further option, at least two of the solid phase synthesis units include single particles having different functionalities attached thereto. In certain embodiments, at least one of the separate first stage reaction vessels includes at least two solid phase synthesis units comprising different functionalities.

The method also includes (b) segregating the solid phase synthesis units into n separate first stage reaction vessels (e.g., flasks, wells of a microwell plate, or the like) in which each separate first stage reaction vessel comprises at least m*f solid phase synthesis units and (c) reacting the solid phase synthesis units in each of the separate first stage reaction vessels with a different first component in the first stage of the synthesis. For example, appropriate reagents are typically added to each reaction vessel to process them in stages. In certain embodiments, each separate first stage reaction vessel in (b) includes m*f solid phase synthesis units. As a further option, at least one of the separate first stage reaction vessels optionally includes at least two solid phase synthesis units having different functionalities attached thereto. Thereafter, the method includes (d) segregating the solid phase synthesis units of (c) into m separate second stage reaction vessels by distributing at least one of the solid phase synthesis units from each of the separate first stage vessels into each separate second stage reaction vessel such that each of the separate second stage reaction vessels comprises at least n*f solid phase synthesis units and (e) reacting the solid phase synthesis units in each of the separate second stage reaction vessels with a different second component in the second stage of the synthesis to synthesize the library of the materials (e.g., a combinatorial chemical library or the like). Distribution is typically performed in a way that each group of supports used in the first stage of synthesis will be divided in m subgroups, and new groups will be created by combining together single subgroups of supports from each group used in the first stage.

In certain embodiments, each of the separate second stage reaction vessels in (d) comprises n*f solid phase synthesis units. Optionally, the solid phase synthesis units of (d) are randomly or non-randomly arranged in at least one of the second stage reaction vessels. Each different first and second component typically independently includes an organic or an inorganic component. The method additionally includes (f) detecting one or more distinguishing physical properties (e.g., different masses or the like) of selected members of the library and (g) identifying the selected members based on the one or more detected distinguishing physical properties.

In alternative embodiments, distribution of solid phase synthesis units from n groups in the first stage of synthesis to m groups, which will be used in the second stage of synthesis may be performed by using two-dimensional arraying. With this technique, supports from each of n groups are arrayed in n columns (or rows) in a two-dimensional matrix. To create m new groups one combines all supports from any f rows (or columns) of the matrix in a group and repeats the process m times. For example, in some embodiments, (b) includes providing one or more of the at least m*f solid phase synthesis units in one or more two-dimensional arrays in the separate first stage reaction vessels, whereas in other embodiments, one or more of the at least m*f solid phase synthesis units in one or more of the separate first stage reaction vessels are non-arrayed. Similarly, in certain embodiments, (d) includes providing one or more of the at least n*f solid phase synthesis units in one or more two-dimensional arrays in the separate second stage reaction vessels, whereas in other embodiments, one or more of the at least n*f solid phase synthesis units in one or more of the separate second stage reaction vessels are non-arrayed.

Figure 8:
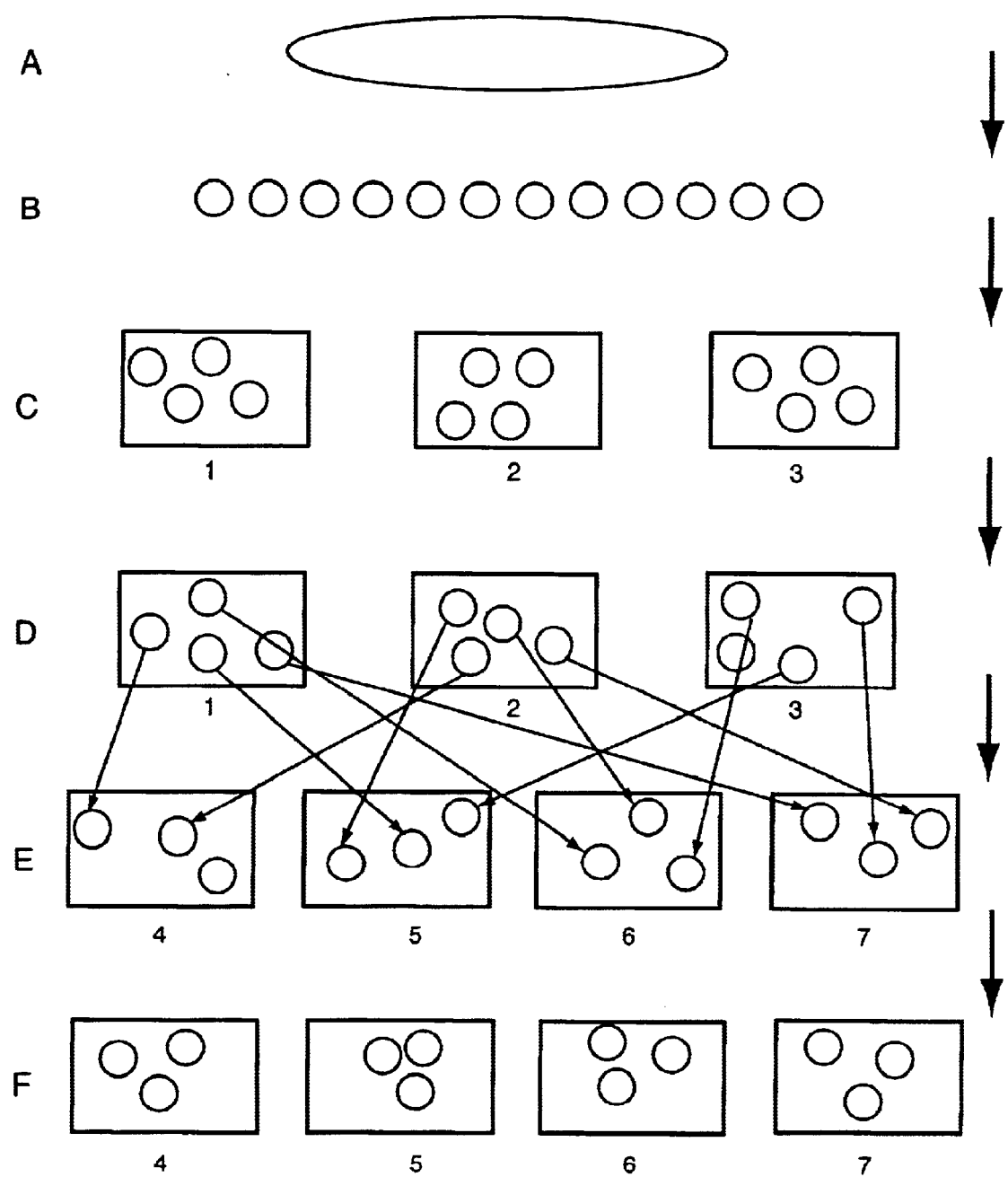
FIG. 8 schematically illustrates a nonredundant split/pool synthesis method.

FIG. 8 schematically illustrates a nonredundant split pool synthesis method which shows synthesis of a hypothetical library produced with two sets of building blocks (3 for the first randomization (R1) and 4 for the second randomization (R2)), with a total complexity of 3×4=12 compounds (i.e., n=3, m=4, and f=1). As shown, resin (depicted in A) is first split into 3×4=12 equal portions and distributed into 12 containers (depicted in B). For example, a suitable container is optionally a tea-bag or other porous container (e.g., any synthesis unit that is composed of inert porous compartments), or an array of the resin. As depicted in C, the containers are pooled in three reaction vessels (according to the number of R1 building blocks, i.e., n=3); thus, each reaction vessel holds four containers. Then, the coupling of the first set of building blocks is performed in each reaction vessel. As depicted in D, the containers are pooled in such a way that each new pool has one container from each of the pools (i.e., reaction vessels) used in C and D. As a result, four new pools are formed (according to the number of R2 building blocks, i.e., m=4) each holding three containers (depicted in E). An advantage of this method is that individual containers do not need to be tracked (e.g., labeled)

during pooling. In this example, the only condition is that one container is taken from each pool in order to ensure that synthesis of all 3×4 compounds is accomplished.

Since containers are not tracked during synthesis, one more step is used for library member identification, namely, identification of the structure of compounds in each container. For example, the mass or molecular weight of a compound can be considered an internal code of a compound as long as there is no redundancy in molecular weights within a set of compounds. Accordingly, synthesis compounds within each vessel (4, 5, 6, 7; depicted in F) have the same R2 and every container has different R1 (see, scheme of pooling depicted in E). Thus, if the set of R1 includes building blocks with different molecular weights, measurement of the molecular weight of a compound from a container within every vessel with known R2 allows for unambiguous determination of R1 and consequently, to identification of the compound.

Typically, the identity of a compound is determined during the quality control step following library synthesis. For example, liquid chromatography/mass spectrometry (LC/MS) experiments with detection of UV absorption is optionally used for analysis of the quality of compounds produced by combinatorial synthesis. In this case the selection of reactants with different molecular weights for use in the first stage of synthesis allows for unambiguous identification of test compounds. Differentiation of test compounds may be facilitated by a comparison of the physical properties of compounds within one group. Compounds which were synthesized using reactants with identical molecular weights in the first stage of synthesis may be differentiated based on differences in chromatographic retention times, different UV absorption, or other quantifiable physical parameters.

Methods of Creating a Shared Chemical History

In carrying out the synthesis, one may initially begin with a number of solid phase synthesis units or particles, e.g., typically at least about 100, more typically at least about 500, and usually at least about 1000. As mentioned, the particles can be functionalized either by a linker for attaching reactants in the first randomization to the solid phase or by certain molecular structures which may be considered as the additional point of diversity for combinatorial compounds.

In one embodiment, particles are divided into as many reaction vessels as there are numbers of choices in the first stage of the relevant synthesis procedure. Appropriate reagents are then added to each reaction vessel to process them in stages. Once the reactions are complete, the solid phase particles are combined into a single pool, followed by the distribution of the resulting mixture into a number of containers. The number of containers equals n*m*f, where n is the number of choices of reactants in the second stage of synthesis, m is the number of choices of reactants in the third stage, and f is a predetermined number of containers, which will have identical chemical history (preferentially f=1). The containers are then be divided into n groups containing m*f containers in each. Each group of n*f containers is placed in a separate reaction vessel.

Figure 9:
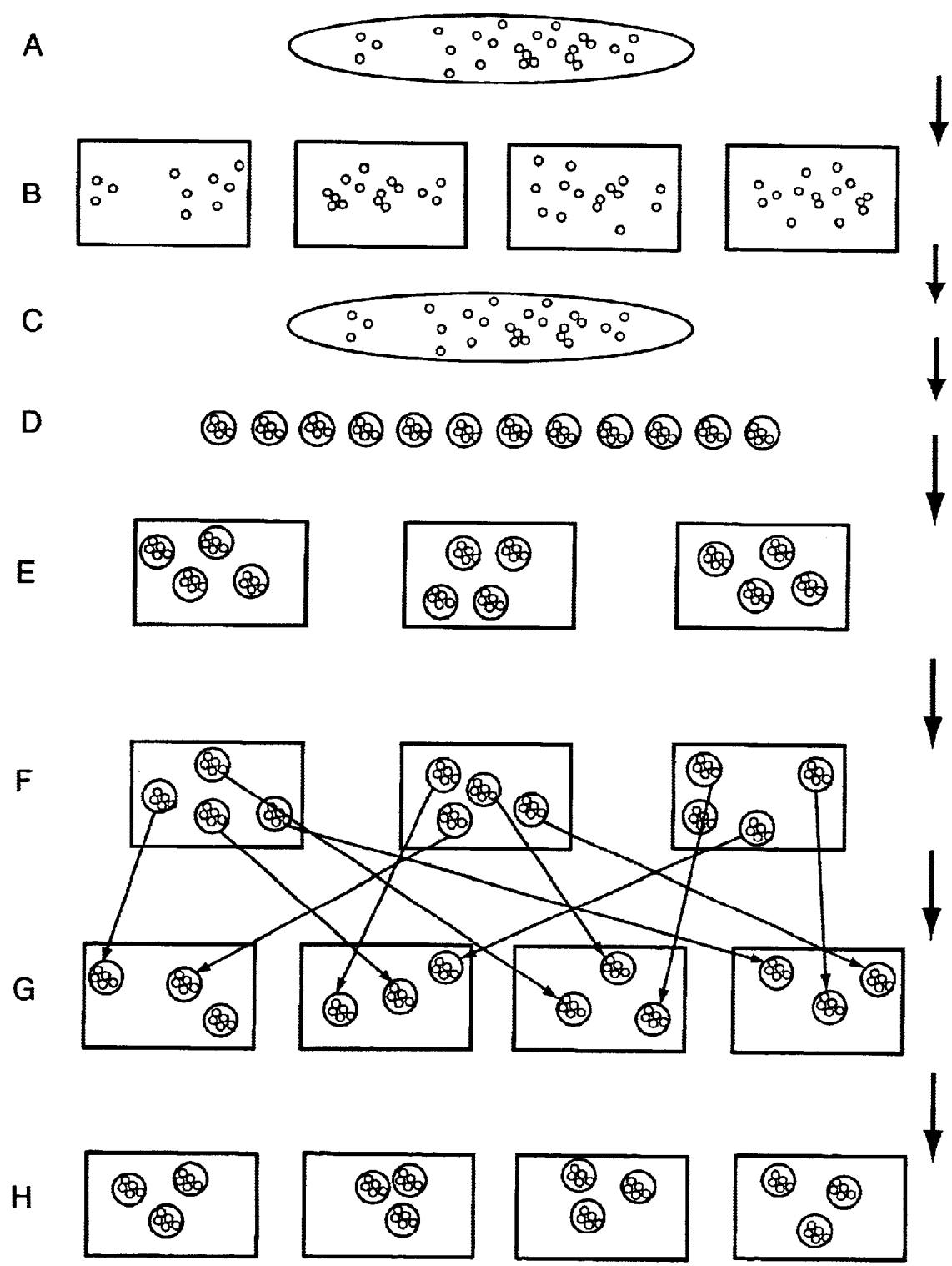
FIG. 9 schematically depicts an embodiment of the nonredundant split/pool synthesis method.

FIG. 9 schematically illustrates the synthesis of a hypothetical library produced with three sets of building blocks (4 for the first randomization (R1), 3 for the second randomization (R2), and four for the third randomization (R3)), with a total complexity of 4×3×4=48 compounds (i.e., n=3, m=4, p=4, and f=1). As shown, resin (depicted in A) is first split into four equal portions (i.e., p=4) and distributed into four reaction vessels, and reactions with first set of building blocks are performed (depicted in B). After reactions are complete, resin is pooled together and mixed (depicted in C). Then resin is divided into 3×4=12 equal portions and distributed into 12 containers (depicted in D). As mentioned, a suitable container optionally includes any synthesis unit that is composed of inert porous wells can be used. Containers are pooled in three reaction vessels (according to the number of R2 building blocks, i.e., n=3), thus each reaction vessel holds four containers (depicted in E). Then, the second set of building blocks is coupled in each respective reaction vessel. Thereafter, containers are pooled in such a way that each new pool has one container from each of the pools (vessels) used in E (depicted in F and G). As a result, four new pools are formed (according to the number of R3 building blocks, i.e., m=4) each holding three containers. Again, containers are not tracked during pooling—the only relevant condition is that one container is taken from each pool in order to ensure synthesis of all compounds. Finally, the third set of building blocks is added to the new pools (depicted in H) and synthesis of a library of 4×3×4 compounds is finished.

In another embodiment, solid phase synthesis units are divided into as many reaction vessels as there are numbers of choices in the first stage. Appropriate reagents are also added to each reaction vessel to process the first stage of synthesis. Once the reactions are complete, the solid phase particles are combined into a single pool, followed by the distribution of the resulting mixture into reaction vessels for the second stage of synthesis. Then, appropriate reagents are added to each reaction vessel to process the second stage of synthesis. Once the reaction(s) is complete, resins are distributed from each of n reaction vessels into m*f number of containers. The total number of containers equals n*m*f, where n is the number of choices of reactants in the second stage of synthesis, m is the number of choices of reactants in the third stage, and f is a predetermined number of containers that will have identical chemistry histories (preferentially f=1). The next step is reshuffling containers from existing n groups into m new groups containing m*f containers in each. Distribution is performed in such a way that each group of containers used in the second stage of synthesis will be divided in m subgroups. New groups will be created by combining together single subgroups of containers from each group used in the second stage. The new groups of containers are then placed in m reaction vessels and the third stage of synthesis is performed. Once the synthesis is complete, the library consists of n*m*f containers, each holding a mixture of solid phase particles with compounds that were synthesized with the same reactants in the second and in the third stage of synthesis but with different reactants in the first stage.

Figure 10:
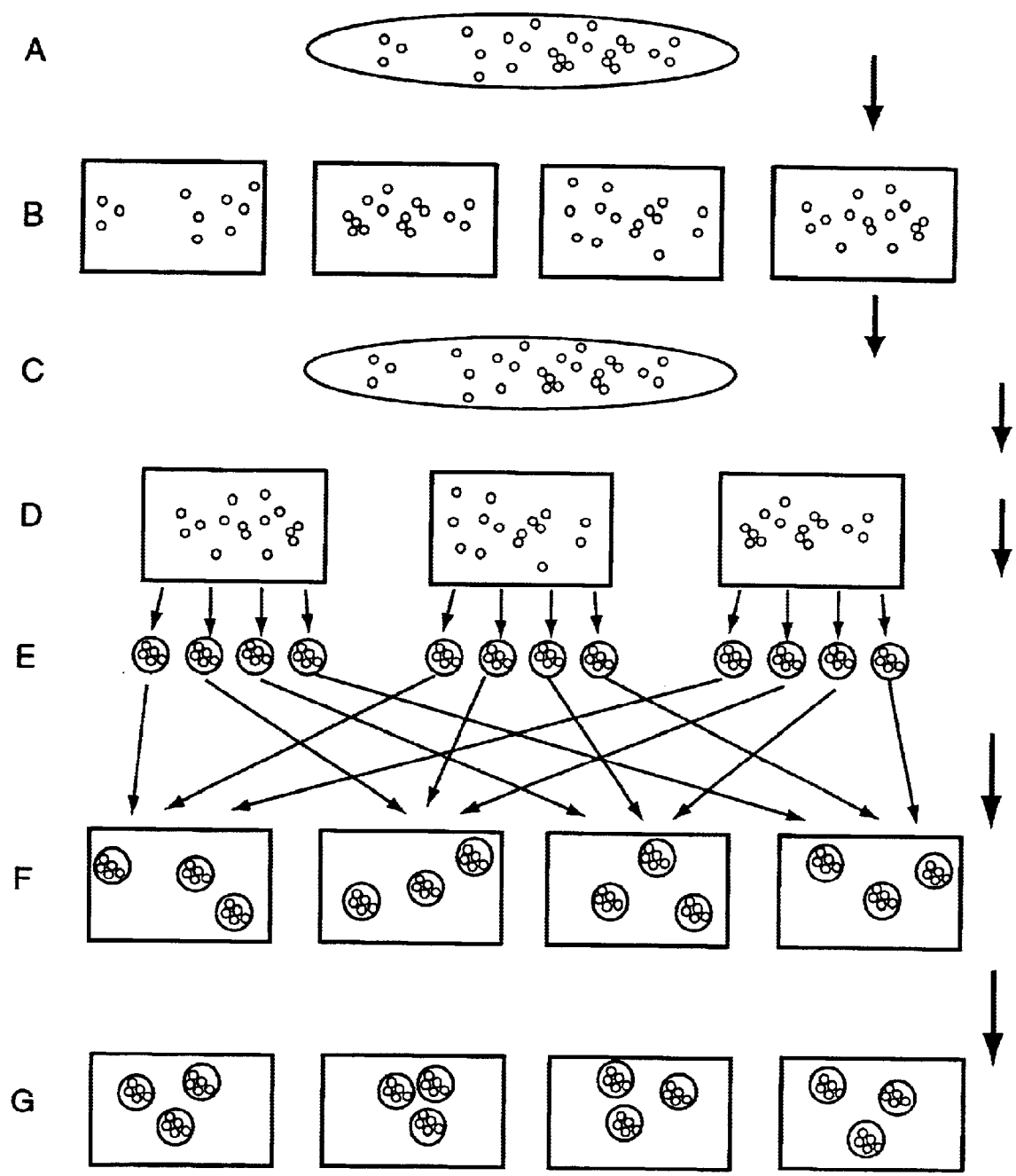
FIG. 10 schematically shows an embodiment of the nonredundant split/pool synthesis method.

FIG. 10 schematically illustrates distributions and redistributions of resin during synthesis of a hypothetical library produced with three sets of building blocks (4 for the first randomization (R1), three for the second randomization (R2), and four for the third randomization (R3)), with a total complexity of 4×3×4=48 compounds (i.e., n=3, m=4, p=4, and f=1). As shown, resin (depicted in A) is first split into four equal portions (i.e., p=4) and distributed into four reaction vessels, and reactions with first set of building blocks are performed (depicted in B). After reactions are complete, resin is pooled together and mixed (depicted in C). Then resin is then divided into three equal portions (i.e., n=3) and placed into reaction vessels for the second stage of the synthesis (depicted in D). Coupling of the second set of building blocks is performed in each reaction vessel correspondingly (depicted in D). Then, resin from each reaction vessel is distributed in three sets of four (i.e., m=4) containers, making 12 containers (depicted in E). As mentioned, any synthesis unit that is composed of inert porous walls can be used as a container. Thereafter, the containers are pooled in such a way that each reaction vessel for the third stage of synthesis has one container originating from each reaction vessel in the second stage of synthesis (depicted in F). Finally the third set of building blocks is added to the new pools (depicted in F) and synthesis of a library of 4×3×4 compounds is finished.

As mentioned, following library synthesis according to any of the methods described herein, physical properties of selected library members are optionally measured in liquid chromatography/mass spectrometry (LC/MS) experiments, which is one of the most frequently used methods for analysis of combinatorial compounds. Any other suitable analysis method is also optionally utilized. In this case, selection of reactants with different molecular weights for use in the first synthesis stage allows the unambiguous identification of test compounds. Compounds which are created using reactants with identical molecular weights in the first stage of synthesis may be differentiated based on differences in retention times in chromatography experiments, UV absorption, or the like.

These and other analytical techniques are described in, e.g., Chu et al. (1993) "Using affinity capillary electrophoresis to identify the peptide in a peptide library that binds most tightly to vancomycin," *J. Org. Chem.* 58:648–652, Fitch et al. (1994) "High-resolution (1)H NMR in solid-phase organic synthesis," *J. Org. Chem.* 59:7955–7956, Gao et al. (1996) "Screening derivatized peptide libraries for tight binding inhibitors to carbonic anhydrase II by electrospray ionization mass spectrometry," *J. Med. Chem.* 39:1949–1955, Keifer (1996) "Influence of resin structure, tether length, and solvent upon the high-resolution (1)H NMR spectra of solid-phase-synthesis resins," *J. Org. Chem.* 61:1558–1559, Metzger et al. (1993) "Ion-spray mass spectrometry and high-performance liquid chromatography. Mass spectrometry of synthetic peptide libraries," *Angew. Chem. Int. Ed.* 32:894–896, Stevanovic and Jung (1993) "Multiple sequence analysis: Pool sequencing of synthetic and natural peptide libraries," *Anal. Biochem.* 212:212–220, and Youngquist et al. (1994) "Matrix-assisted laser desorption ionization for rapid determination of the sequences of biologically active peptides isolated from support-bound combinatorial peptide libraries," *Rapid Commun. Mass Spectrom.* 8:77–81. Structural identification is described further below.

Solid Phase Synthesis Units

The solid phase synthesis units utilized in the methods of the invention include many alternative embodiments. For example, the solid phase synthesis units optionally each include a single particle independently selected from, e.g., a bead, a crown, a piece of paper, a piece of cotton, a piece of polymer, or the like. Optionally, the solid phase synthesis units each include multiple particles combined together. For example, an array or a container optionally includes multiple particles combined together. In certain embodiments, at least one of the multiple particles includes a non-functionalized solid support, whereas in others, at least one of the multiple particles includes a solid support having one or more functionalities attached thereto. In some embodiments, at least two of the multiple particles include solid supports having one or more identical or different functionalities attached thereto. Additional details regarding solid phase synthesis units are found in co-filed application "Nonredundant Split/ Pool Synthesis of Combinatorial Libraries" by Sepetov et al., U.S. Ser. No. 09/776,233.

Linkers and Linking Chemistries

The chemical components of the invention are optionally presented on solid or semi-solid supports via any of a variety of linking chemistries (they are, alternately, directly attached to the supports, e.g., by any available chemical or physical method), allowing the incorporation of biological and chemical components of interest into the solid supports. A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed include papers, ceramics, such as glass, metals, metalloids, semiconductive materials, cements, or the like. In addition, substances that form gels, such as proteins (e.g., gelatins), lipopolysaccharides, silicates, agarose and are also optionally used.

A wide variety of linking chemistries are available for linking molecules to a wide variety of solid or semi-solid support elements. It is impractical and unnecessary to describe all of the possible known linking chemistries for linking molecules to a solid support. It is expected that one of skill can easily select appropriate chemistries, depending on the intended application. Further details regarding linkers and linking chemistries are found in co-filed application "Nonredundant Split/Pool Synthesis of Combinatorial Libraries" by Sepetov et al., U.S. Ser. No. 09/776,233.

Components and Library of Materials

Essentially any organic or inorganic compound is optionally formed according to the methods described herein. As a consequence, no attempt is made herein to describe all of the possible reagents or components, or combinatorial compounds optionally utilized and/or synthesized. However, for purposes of illustration, but not for limitation, certain general classes of reagents and/or combinatorial compounds are mentioned as follows.

Organic compounds include of carbon and hydrogen, with or without oxygen, nitrogen or other elements, except those in which carbon does not play a critical role (e.g., carbonate salts). Examples of organic compounds that are optionally synthesized using the methods described herein include, but are not limited to, biological (nucleic acids, peptides, polypeptides, lipids, carbohydrates, or the like) or non-biological polymers. Polymers include, e.g., nonmetallic materials that include large macromolecules composed of many repeating units. These materials are optionally natural or synthetic and cross-linked or non-crosslinked. They are optionally homopolymers, copolymers, or higher-ordered polymers. Examples of polymers that are optionally prepared using the methods of the present invention include, but are not limited to, the following: polyurethanes, polyesters, polycarbonates, polyethyleneimines, polyacetates, polystyrenes, polyamides, polyanilines, polyacetylenes, polypyrroles, or the like. Organometallic compounds are also optionally prepared using the methods of the present invention. These include a class of compounds of the type R-M in which carbon atoms are linked directly with metal atoms.

In contrast, inorganic compounds do not contain carbon as a principal element. The oxides and sulphides of carbon and the metallic carbides are considered inorganic materials. Additional examples of inorganic compounds that are optionally synthesized using the methods described herein include, but are not limited to, intermetallics, metal alloys, ceramics, and magnetic alloys.

Various composite materials are also optionally prepared according to the methods described herein. Composite materials include, e.g., any combination of two materials differing in form or composition on a macroscale. They are optionally inorganic, organic or a combination thereof. They also include, e.g., doped materials, dispersed metal catalysts and other heterogeneous solids.

The reagents and/or combinatorial compounds of the invention are typically covalent network solids, ionic solids, or moleculare solids. A covalent network solid typically includes atoms held together in a large network of chains by covalent bonds. An ionic solid is generally modeled as cations and anions held together by electrical attraction of opposite charge. Finally, a molecular solid typically includes atoms or molecules held together by intermolecular forces.

Computer Program Products

The present invention also provides a computer program product that includes a computer readable medium having one or more logic instructions for (a) correlating molecular mass measurements of two or more chemical or physical library members having a shared chemical history to two or more virtual masses in a logical matrix to identify one or more groups of virtual masses that most likely describe chemical or physical transformations undergone by the two or more chemical or physical library members. The computer program product also includes one or more logic instructions for (b) identifying predicted or actual structures of the two or more chemical or physical library members within the one or more identified groups based one the molecular mass measurements. The correlations generally account for one or more mass defects of reaction. The computer readable medium optionally includes one or more of: a CD-ROM, a floppy disk, a tape, a flash memory device or component, a system memory device or component, a hard drive, or a data signal embodied in a carrier wave.

Kits

The present invention also provides kits that typically include systems, system software, modules, and workstations for performing the combinatorial synthetic and structural identification methods described herein. In certain embodiments, a kit includes only system software, as described above ("Computer Program Products"). A kit optionally contains additional components for the assembly and/or operation of a multimodule workstation of the invention including, but not restricted to robotic elements (e.g., a track robot, a robotic armature, or the like), reagent, solid phase synthesis unit, and/or reaction vessel handling devices, and computers (including, e.g., input/output devices, CPUs, or the like). Kits are optionally packaged to include reagents, control/calibrating materials, solid phase synthesis units, and/or reaction vessels for performing the methods of the invention. In the case of pre-packaged reagents, the kits optionally include pre-measured or pre-dosed reagents that are ready to incorporate into the synthetic methods without measurement, e.g., pre-measured fluid aliquots, or pre-weighed or pre-measured solid reagents that can be easily reconstituted by the end-user of the kit. Generally, reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like. Kits typically include appropriate instructions for using the reagents, practicing the methods, and operating the systems. Kits also typically include packaging materials or containers for holding kit components.

EXAMPLES

Example 1

Structural Identification and Combinatorial Synthesis System

Figure 11:
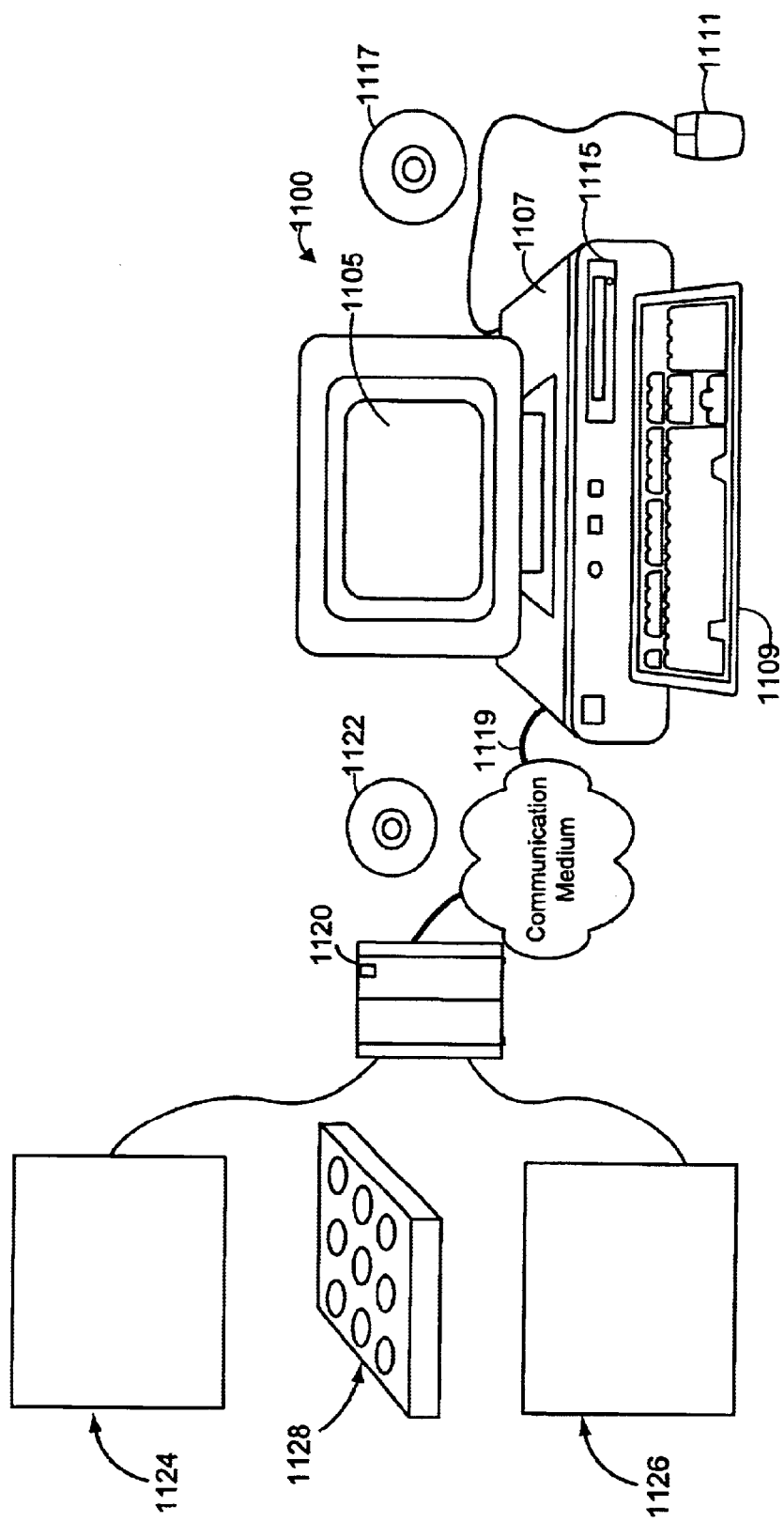
FIG. 11 is a block diagram showing a representative example structural identification and combinatorial synthesis system including a logic device in which various aspects of the present invention may be embodied.

FIG. 11 is a schematic showing a representative example structural identification and combinatorial synthesis system including a logic device in which various aspects of the present invention may be embodied. As will be understood by practitioners in the art from the teachings provided herein, the invention is optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform according to the invention. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 11 shows information appliance or digital device 1100 that may be understood as a logical apparatus that can read instructions from media 1117 and/or network port 1119, which can optionally be connected to server 1120 having fixed media 1122. Apparatus 1100 can thereafter use those instructions to direct server or client logic, as understood in the art, to embody aspects of the invention. One type of logical apparatus that may embody the invention is a computer system as illustrated in 1100, containing CPU 1107, optional input devices 1109 and 1111, disk drives 1115 and optional monitor 1105. Fixed media 1117, or fixed media 1122 over port 1119, may be used to program such a system and may represent a disk-type optical or magnetic media, magnetic tape, solid state dynamic or static memory, or the like. In specific embodiments, the invention may be embodied in whole or in part as software recorded on this fixed media. Communication port 1119 may also be used to initially receive instructions that are used to program such a system and may represent any type of communication connection. Optionally, the invention is embodied in whole or in part within the circuitry of an application specific integrated circuit (ACIS) or a programmable logic device (PLD). In such a case, the invention may be embodied in a computer understandable descriptor language, which may be used to create an ASIC, or PLD.

FIG. 11 also includes handling system 1124 and detection system 1126, both of which are operably connected to digital device 1100 via server 1120. Optionally, handling system 1124 and/or detection system 1126 are directly connected to digital device 1100. During operation, handling system 1124 typically distributes reagents and/or solid phase synthesis units (e.g., individual beads, tea-bags, or other reaction containers) to various reaction vessels, such as microwell plate 1128 which includes a plurality of reaction vessels (i.e., wells) disposed therein. Between synthetic steps, handling system 1124 generally pools and/or segregates solid phase synthesis units for additional rounds of synthesis or for product analysis.

Detection system 1126 generally includes a mass spectrometer for detecting masses of selected members of a combinatorial library following synthesis. Digital device 1100 digitizes, stores, and manipulates signal information detected by detection system 1126 using one or more logic instructions. In preferred embodiments, system software operating in digital device 1100 correlates detected masses of synthesized library members with a logical matrix of virtual masses stored on, e.g., fixed media 1117 or on fixed media 1122 to identify structures corresponding to selected synthesized library members.

Example 2
Sequential Logical Exclusion-Based Structural Identification Description of Library A combinatorial library was synthesized using split/pool technology in which twenty building blocks (R1) with molecular weights, 59, 73, 87, 97, 99, 107, 108, 114, 127, 128, 137, 142, 143, 144, 155, 157, 167, 179, 181, and 183 were used for the first randomization. After the first randomization, the solid phase particle were combined, reacted with a scaffold with a molecular weight of 147 and distributed for the second randomization step. Twenty-one building blocks (R2) with molecular weights 57, 59, 73, 87, 97, 99, 107, 108, 114, 127, 128, 137, 142, 143, 144, 155, 157, 167, 179, 181, and 183 were used for second randomization. No subsequent pooling of solid phase particles was performed; thus, compounds in each of the pools after the second randomization may be described as having a shared chemical history because they experienced the same chemical transformation (reaction with scaffold and coupling of one R2(s)). The molecular weights of all compounds in the resulting library can be calculated by summing the molecular weights of the building blocks used in the first and the second randomization and by adding constant value (147) of the scaffolding present in all compounds. The results of these calculations are presented in Table 1. Each row in Table 1 contains the predicted molecular weights of compounds that were created using common building block in the first randomization step. Each column in the Table 1 contains the predicted molecular weights of compounds created using a common building block in the second randomization step.

Structural Identification

In this example the identity of the building block used in both the first and second randomization for each individual compound in unknown. However, since the compounds in each pool after the second randomization can be described as having a shared chemical history, $\Delta mw$ of compounds before and after the second randomization should be equal for all compounds within each group.

In this example two compounds of unknown structure were taken form one of the twenty-one groups in the second randomization and analyzed by mass spectroscopy, resulting in two molecular weights: 401 and 334. By itself the molecular weight of each individual does not provide enough information for unambiguous structure identification. Nine different possible combinations of building blocks in the first and second randomization produce a compound with a molecular weight of 401, and four combinations produce a compound with a molecular weight of 334 (highlighted in Table 2). However, the fact that the compounds were grouped during the second randomization makes structure elucidation unambiguous.

Beginning the analysis with molecular weight 401, one can choose for further consideration only nine columns in Table 1 which contain 401. These columns correspond to R203, R204, R205, R206, R210, R216, R217, R218, and R220 building blocks used for the second randomization. Among all compounds contained in these nine columns only one compound matches a molecular weight of 334. This molecular weight fits to the combination of R108 and R203 building blocks used in the first and the second randomization. According to the synthesis scheme, both compounds with molecular weight 334 and 401 have the same building block in the second randomization; thus, the compound with molecular weight 401 was unambiguously synthesized using building blocks R119 and R203. The identical assignment of building blocks to molecular weight 334 and 401 will be obtained when starting the analysis using a molecular weight of 334.

Moreover, analysis of Table 2 shows that not more than 5 different compounds from any group of compounds with a shared chemical history are necessary for unambiguous assignments of the building blocks used for synthesis of all compounds in this library.

Example 3
Statistics-Based Structural Identification

This is an example of the utilization of a statistics-based structural identification method for data derived from compounds with a shared chemical history from the same combinatorial library described in Example 2 above.

Figure 12:
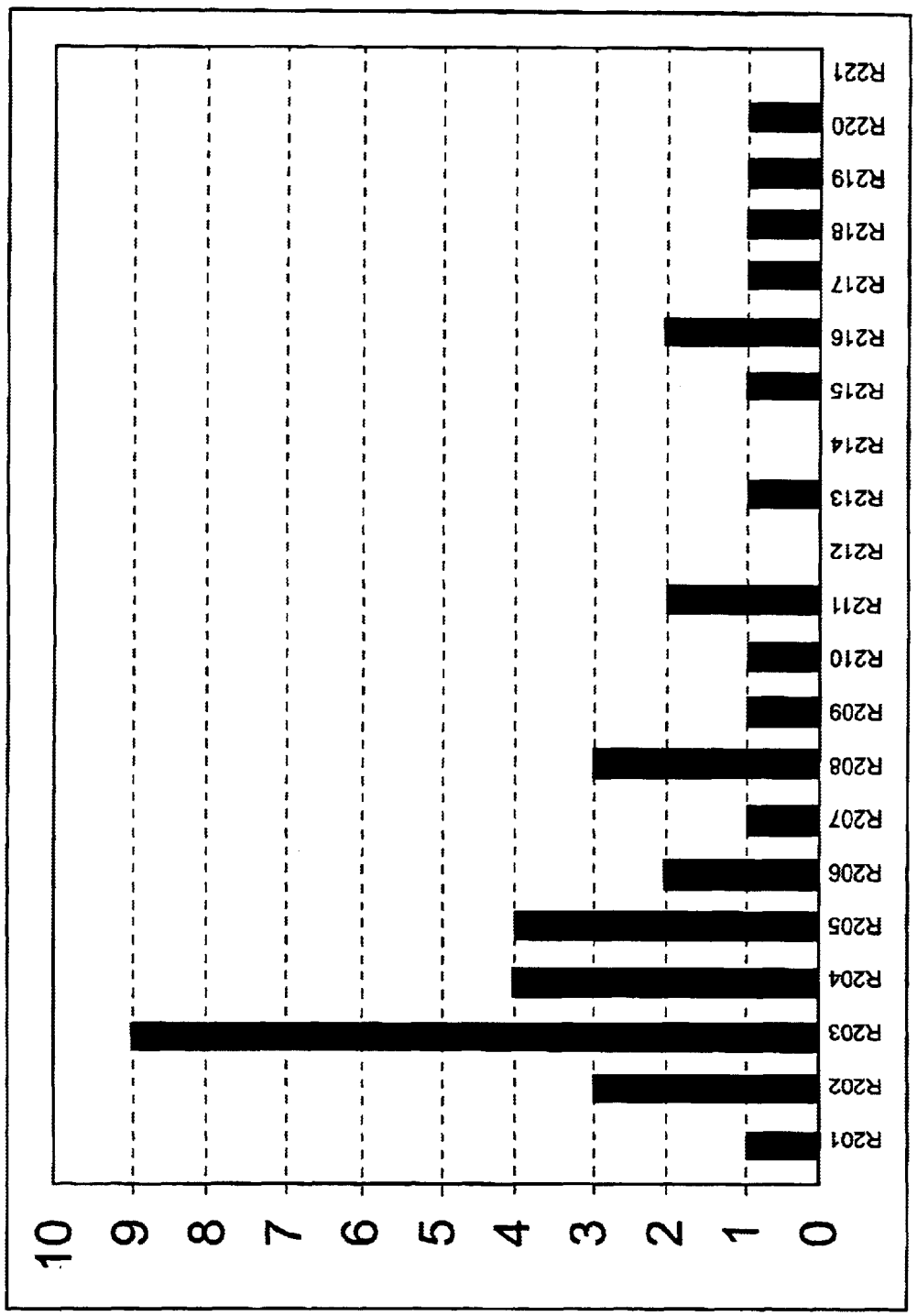
FIG. 12 is a histogram of the distribution of P variable generated in Example 3 of the invention.

In this example ten compounds presented for analysis showed molecular weights 293, 303, 307, 317, 319, 328, 334, 362, 399, and 401. Analysis starts with P variable equal to zero for all groups of calculated molecular weights. Matching 293 with all calculated molecular weights allows increasing P variables for columns corresponding to R202, R203, and R204. The next value for matching, 303, will increase P variables for columns R201, R202, and R205. The only common column, which matches both 293 and 303, is the column corresponding to R202. Thus, utilization of the method described in example 2 will point to R202. However, continuation of the analysis by this statistical method using all data available for analysis will reveal that R203 satisfies the most data. The last line in Table 3 presents the final values of P. A histogram of the distribution of P variables is presented in FIG. 12.

Figure 13:
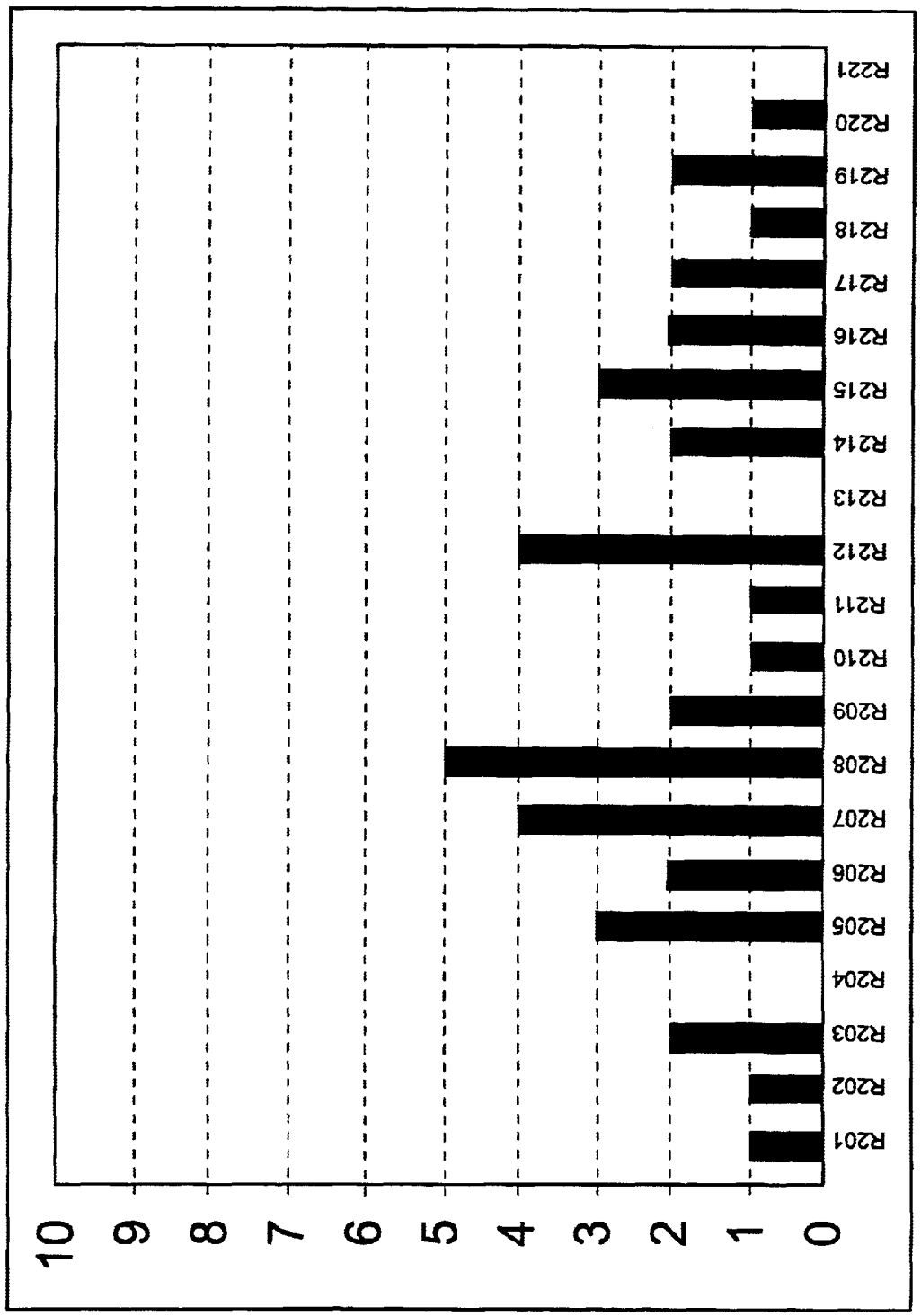
FIG. 13 is a histogram showing results from the utilization of the statistics-based structural identification method illustrated in Example 3.
Figure 14:
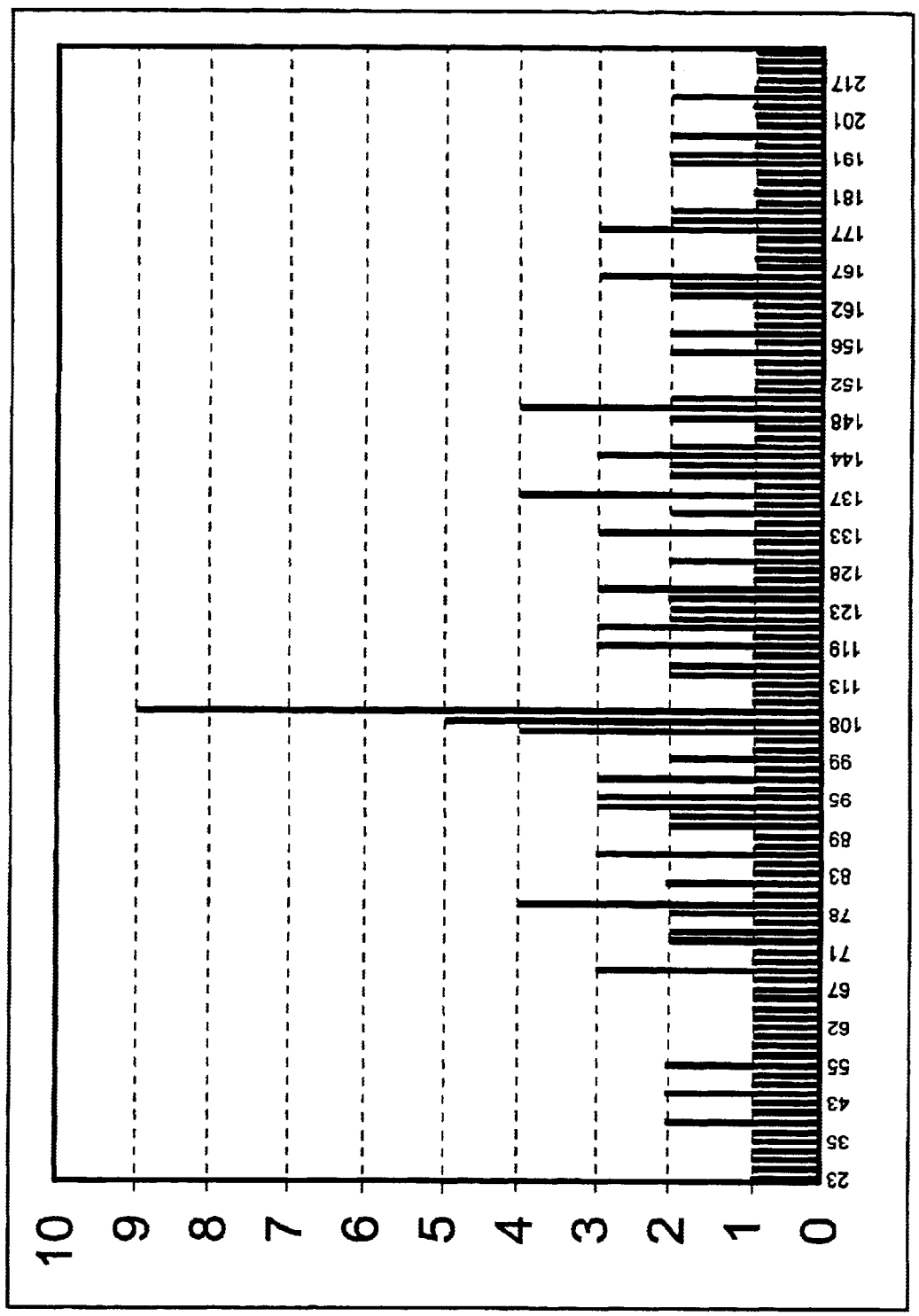
FIG. 14 is the histogram of P variables resulting from a set of virtual mass change values in Example 4.

Example 4
Statistics-Based Structural Identification Involving Virtual Mass Changes This is an example of utilization of the statistics-based structural identification method involving virtual mass changes for data derived from compounds with a shared chemical history from the same combinatorial library as described in Examples 2 and 3 above. In this example ten compounds presented for analysis showed molecular weights 353, 363, 369, 383, 398, 399, 411, 423, 435, and 439. The result of the utilization of this statistical method for this set of data is presented on FIG. 13 and shows that no more than 5 values from this group can be described as originating form compounds with shared chemical history. This result allows hypothesizing that a side reaction(s) occurred. This data set was analyzed by the statistical method where a set of virtual $\Delta mw(s)$ was created using all ten molecular weights obtained from compounds presented for analysis and 20 molecular weights of R1. Thus, a set of virtual $\Delta mw$ was obtained which contained 120 values. In the next step, P variables were calculated for each virtual $\Delta mw$. The resulting histogram is presented in FIG. 14 and shows that 9 out of 10 molecular weights originating from compounds considered in this example may be described as one group of compounds which experienced common chemical transformation that resulted in change of molecular weights equal to 256, corresponding to transformation of an initial set of MW by a building block in the second randomization with a mass of 109.

Example 5
Simultaneous System of Equations

In this example, four building blocks were used for the first randomization of a split/pool library. The sum of the molecular weights of all four building blocks equaled 412. After the first randomization step, the solid phase particles were combined, mixed and reacted with an unknown reagent. Mass spectrometric analysis after the reactions revealed four different compounds with molecular weights 179, 193, 221, and 235. What were the molecular weights of the compounds before reaction and what is the difference in some molecular weights of the compounds before and after the reaction if we consider the compounds as a group of compounds with SCH? Since the molecular weight of a product of reaction may be described by the equation $x+y=a$, we can easily write four equations based on the molecular weights of the found products, as follows: $x1+y=179$, $x2+y=193$, $x3+y=221$, and $x4+y=235$. The fifth equation is determined by the design of the library, knowing the reagents which were used to create the first randomization, as follows: $x1+x2+x3+x4=412$. Solving this system of 5 equations with 5 unknowns yields the unambiguous solution: $x1=75$, $x2=89$, $x3=117$, $x4=131$, and $y=104$. Thus, a full description of all subsequent compounds may be achieved using limited knowledge about the building blocks used for the first randomization without prior knowledge about the reagent used for the second randomization (transformation).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

TABLE 1

Molecular weights of compounds in combinatorial library

| | | 57 R201 | 59 R202 | 73 R203 | 87 R204 | 97 R205 | 99 R206 | 107 R207 | 108 R208 | 114 R209 | 127 R210 | 128 R211 | 137 R212 | 142 R213 |
|---|---|---|---|---|---|---|---|---|---|---|---|---|---|---|
| 59 | R101 | 263 | 265 | 279 | 293 | 303 | 305 | 313 | 314 | 320 | 333 | 334 | 343 | 348 |
| 73 | R102 | 277 | 379 | 293 | 307 | 317 | 319 | 327 | 328 | 334 | 347 | 348 | 357 | 362 |
| 87 | R103 | 291 | 293 | 307 | 321 | 331 | 333 | 341 | 342 | 348 | 361 | 362 | 371 | 376 |
| 97 | R104 | 301 | 303 | 317 | 331 | 341 | 343 | 351 | 352 | 358 | 371 | 372 | 381 | 386 |
| 99 | R105 | 303 | 305 | 319 | 333 | 343 | 345 | 353 | 354 | 360 | 373 | 374 | 383 | 388 |
| 107 | R106 | 311 | 313 | 327 | 341 | 351 | 353 | 361 | 362 | 368 | 381 | 382 | 391 | 396 |
| 108 | R107 | 312 | 314 | 328 | 342 | 352 | 354 | 362 | 363 | 369 | 382 | 383 | 392 | 397 |
| 114 | R108 | 318 | 320 | 334 | 348 | 358 | 360 | 368 | 369 | 375 | 388 | 389 | 398 | 403 |
| 127 | R109 | 331 | 333 | 347 | 361 | 371 | 373 | 381 | 382 | 388 | 401 | 402 | 411 | 416 |
| 128 | R110 | 332 | 334 | 348 | 362 | 372 | 374 | 382 | 383 | 389 | 402 | 403 | 412 | 417 |
| 137 | R111 | 341 | 343 | 357 | 371 | 381 | 383 | 391 | 392 | 398 | 411 | 412 | 421 | 426 |
| 142 | R112 | 346 | 348 | 362 | 376 | 386 | 388 | 396 | 397 | 403 | 416 | 417 | 426 | 431 |
| 143 | R113 | 347 | 349 | 363 | 377 | 387 | 389 | 397 | 398 | 404 | 417 | 418 | 427 | 432 |
| 144 | R114 | 348 | 350 | 364 | 378 | 388 | 390 | 398 | 399 | 405 | 418 | 419 | 428 | 433 |
| 155 | R115 | 359 | 361 | 375 | 389 | 399 | 401 | 409 | 410 | 416 | 429 | 430 | 439 | 444 |
| 157 | R116 | 361 | 363 | 377 | 391 | 401 | 403 | 411 | 412 | 418 | 431 | 432 | 441 | 446 |
| 167 | R117 | 371 | 373 | 387 | 401 | 411 | 413 | 421 | 422 | 428 | 441 | 442 | 451 | 456 |
| 179 | R118 | 383 | 385 | 399 | 413 | 423 | 425 | 433 | 434 | 440 | 453 | 454 | 463 | 468 |
| 181 | R119 | 385 | 387 | 401 | 415 | 425 | 427 | 435 | 436 | 442 | 455 | 456 | 465 | 470 |
| 183 | R120 | 387 | 389 | 403 | 417 | 427 | 429 | 437 | 438 | 444 | 457 | 458 | 467 | 472 |

| | | 143 R214 | 144 R215 | 155 R216 | 157 R217 | 167 R218 | 179 R219 | 181 R220 | 183 R221 |
|---|---|---|---|---|---|---|---|---|---|
| 59 | R101 | 349 | 350 | 361 | 363 | 373 | 385 | 387 | 389 |
| 73 | R102 | 363 | 364 | 375 | 377 | 387 | 399 | 401 | 403 |
| 87 | R103 | 377 | 378 | 389 | 391 | 401 | 413 | 415 | 417 |
| 97 | R104 | 387 | 388 | 399 | 401 | 411 | 423 | 425 | 427 |
| 99 | R105 | 389 | 390 | 401 | 403 | 413 | 425 | 427 | 429 |
| 107 | R106 | 397 | 398 | 409 | 411 | 421 | 433 | 435 | 437 |
| 108 | R107 | 398 | 399 | 410 | 412 | 422 | 434 | 436 | 438 |
| 114 | R108 | 404 | 405 | 416 | 418 | 428 | 440 | 442 | 444 |
| 127 | R109 | 417 | 418 | 429 | 431 | 441 | 453 | 455 | 457 |
| 128 | R110 | 418 | 419 | 430 | 432 | 442 | 454 | 456 | 458 |
| 137 | R111 | 427 | 428 | 439 | 441 | 451 | 463 | 465 | 467 |
| 142 | R112 | 432 | 433 | 444 | 446 | 456 | 468 | 470 | 472 |
| 143 | R113 | 433 | 434 | 445 | 447 | 457 | 469 | 471 | 473 |
| 144 | R114 | 434 | 435 | 446 | 448 | 458 | 470 | 472 | 474 |
| 155 | R115 | 445 | 446 | 457 | 459 | 469 | 481 | 483 | 485 |
| 157 | R116 | 447 | 448 | 459 | 461 | 471 | 483 | 485 | 487 |
| 167 | R117 | 457 | 458 | 469 | 471 | 481 | 493 | 495 | 497 |
| 179 | R118 | 469 | 470 | 481 | 483 | 493 | 505 | 507 | 509 |
| 181 | R119 | 471 | 472 | 483 | 485 | 495 | 507 | 509 | 511 |
| 183 | R120 | 473 | 474 | 485 | 487 | 497 | 509 | 511 | 513 |

TABLE 2

| | | 57<br>R201 | 59<br>R202 | 73<br>R203 | 87<br>R204 | 97<br>R205 | 99<br>R206 | 107<br>R207 | 108<br>R208 | 114<br>R209 | 127<br>R210 | 128<br>R211 | 137<br>R212 | 142<br>R213 | 143<br>R214 | 144<br>R215 | 155<br>R216 | 157<br>R217 | 167<br>R218 | 179<br>R219 | 181<br>R220 | 183<br>R221 |
|---|---|---|---|---|---|---|---|---|---|---|---|---|---|---|---|---|---|---|---|---|---|---|
| 59 | R101 | 263 | 265 | 279 | 293 | 303 | 305 | 313 | 314 | 320 | 333 | 334 | 343 | 348 | 349 | 350 | 361 | 363 | 373 | 385 | 387 | 389 |
| 73 | R102 | 277 | 379 | 293 | 307 | 317 | 319 | 327 | 328 | 334 | 347 | 348 | 357 | 362 | 363 | 364 | 375 | 377 | 387 | 399 | 401 | 403 |
| 87 | R103 | 291 | 293 | 307 | 321 | 331 | 333 | 341 | 342 | 348 | 361 | 362 | 371 | 376 | 377 | 378 | 289 | 391 | 401 | 413 | 415 | 417 |
| 97 | R104 | 301 | 303 | 317 | 331 | 341 | 343 | 351 | 352 | 358 | 371 | 372 | 381 | 386 | 387 | 388 | 399 | 401 | 411 | 423 | 425 | 427 |
| 99 | R105 | 303 | 305 | 319 | 333 | 343 | 345 | 353 | 354 | 360 | 373 | 374 | 383 | 388 | 389 | 390 | 401 | 403 | 413 | 425 | 427 | 429 |
| 107 | R106 | 311 | 313 | 327 | 341 | 351 | 353 | 361 | 362 | 368 | 381 | 382 | 391 | 396 | 397 | 398 | 409 | 411 | 421 | 433 | 435 | 437 |
| 108 | R107 | 312 | 314 | 328 | 342 | 352 | 354 | 362 | 363 | 369 | 382 | 383 | 392 | 397 | 398 | 399 | 410 | 412 | 422 | 434 | 436 | 438 |
| 114 | R108 | 318 | 320 | 334 | 348 | 358 | 360 | 368 | 369 | 375 | 388 | 389 | 398 | 403 | 404 | 405 | 416 | 418 | 428 | 440 | 442 | 444 |
| 127 | R109 | 331 | 333 | 347 | 361 | 371 | 373 | 381 | 382 | 388 | 401 | 402 | 411 | 416 | 417 | 418 | 429 | 431 | 441 | 453 | 455 | 457 |
| 128 | R110 | 332 | 334 | 348 | 362 | 372 | 374 | 382 | 383 | 389 | 402 | 403 | 412 | 417 | 418 | 419 | 430 | 432 | 442 | 454 | 456 | 458 |
| 137 | R111 | 341 | 343 | 357 | 371 | 381 | 383 | 391 | 392 | 398 | 411 | 412 | 421 | 426 | 427 | 428 | 439 | 441 | 451 | 463 | 465 | 467 |
| 142 | R112 | 346 | 348 | 362 | 376 | 386 | 388 | 396 | 397 | 403 | 416 | 417 | 426 | 431 | 432 | 433 | 444 | 446 | 456 | 468 | 470 | 472 |
| 143 | R113 | 347 | 349 | 363 | 377 | 387 | 389 | 397 | 398 | 404 | 417 | 418 | 427 | 432 | 433 | 434 | 445 | 447 | 457 | 469 | 471 | 473 |
| 144 | R114 | 348 | 350 | 364 | 378 | 388 | 390 | 398 | 399 | 405 | 418 | 419 | 428 | 433 | 434 | 435 | 446 | 448 | 458 | 470 | 472 | 474 |
| 155 | R115 | 359 | 361 | 375 | 389 | 399 | 401 | 409 | 410 | 416 | 429 | 430 | 439 | 444 | 445 | 446 | 457 | 459 | 469 | 481 | 483 | 485 |
| 157 | R116 | 361 | 363 | 377 | 391 | 401 | 403 | 411 | 412 | 418 | 431 | 432 | 441 | 446 | 447 | 448 | 459 | 461 | 471 | 483 | 485 | 487 |
| 167 | R117 | 371 | 373 | 387 | 401 | 411 | 413 | 421 | 422 | 428 | 441 | 442 | 451 | 456 | 457 | 458 | 469 | 471 | 481 | 493 | 495 | 497 |
| 179 | R118 | 383 | 385 | 399 | 413 | 423 | 425 | 433 | 434 | 440 | 453 | 454 | 463 | 458 | 469 | 470 | 481 | 483 | 493 | 505 | 507 | 509 |
| 181 | R119 | 385 | 387 | 401 | 415 | 425 | 427 | 435 | 436 | 442 | 455 | 456 | 465 | 470 | 471 | 472 | 483 | 485 | 495 | 507 | 509 | 511 |
| 183 | R120 | 387 | 389 | 403 | 417 | 427 | 429 | 437 | 438 | 444 | 457 | 458 | 467 | 472 | 472 | 474 | 485 | 487 | 497 | 509 | 511 | 513 |

TABLE 3

| | | 57<br>R201 | 59<br>R202 | 73<br>R203 | 87<br>R204 | 97<br>R205 | 99<br>R206 | 107<br>R207 | 108<br>R208 | 114<br>R209 | 127<br>R210 | 128<br>R211 | 137<br>R212 | 142<br>R213 | 143<br>R214 | 144<br>R215 | 155<br>R216 | 157<br>R217 | 167<br>R218 | 179<br>R219 | 181<br>R220 | 183<br>R221 |
|---|---|---|---|---|---|---|---|---|---|---|---|---|---|---|---|---|---|---|---|---|---|---|
| 59 | R101 | 263 | 265 | 279 | 293 | 303 | 305 | 313 | 314 | 320 | 333 | 334 | 343 | 348 | 349 | 350 | 361 | 363 | 373 | 385 | 387 | 389 |
| 73 | R102 | 277 | 379 | 293 | 307 | 317 | 319 | 327 | 328 | 334 | 347 | 348 | 357 | 362 | 363 | 364 | 375 | 377 | 387 | 399 | 401 | 403 |
| 87 | R103 | 291 | 293 | 307 | 321 | 331 | 333 | 341 | 342 | 348 | 361 | 362 | 371 | 376 | 377 | 378 | 289 | 391 | 401 | 413 | 415 | 417 |
| 97 | R104 | 301 | 303 | 317 | 331 | 341 | 343 | 351 | 352 | 358 | 371 | 372 | 381 | 386 | 387 | 388 | 399 | 401 | 411 | 423 | 425 | 427 |
| 99 | R105 | 303 | 305 | 319 | 333 | 343 | 345 | 353 | 354 | 360 | 373 | 374 | 383 | 388 | 389 | 390 | 401 | 403 | 413 | 425 | 427 | 429 |
| 107 | R106 | 311 | 313 | 327 | 341 | 351 | 353 | 361 | 362 | 368 | 381 | 382 | 391 | 396 | 397 | 398 | 409 | 411 | 421 | 433 | 435 | 437 |
| 108 | R107 | 312 | 314 | 328 | 342 | 352 | 354 | 362 | 363 | 369 | 382 | 383 | 392 | 397 | 398 | 399 | 410 | 412 | 422 | 434 | 436 | 438 |
| 114 | R108 | 318 | 320 | 334 | 348 | 358 | 360 | 368 | 369 | 375 | 388 | 389 | 398 | 403 | 404 | 405 | 416 | 418 | 428 | 440 | 442 | 444 |
| 127 | R109 | 331 | 333 | 347 | 361 | 371 | 373 | 381 | 382 | 388 | 401 | 402 | 411 | 416 | 417 | 418 | 429 | 431 | 441 | 453 | 455 | 457 |
| 128 | R110 | 332 | 334 | 348 | 362 | 372 | 374 | 382 | 383 | 389 | 402 | 403 | 412 | 417 | 418 | 419 | 430 | 432 | 442 | 454 | 456 | 458 |
| 137 | R111 | 341 | 343 | 357 | 371 | 381 | 383 | 391 | 392 | 398 | 411 | 412 | 421 | 426 | 427 | 428 | 439 | 441 | 451 | 463 | 465 | 467 |
| 142 | R112 | 346 | 348 | 362 | 376 | 386 | 388 | 396 | 397 | 403 | 416 | 417 | 426 | 431 | 432 | 433 | 444 | 446 | 456 | 468 | 470 | 472 |
| 143 | R113 | 347 | 349 | 363 | 377 | 387 | 389 | 397 | 398 | 404 | 417 | 418 | 427 | 432 | 433 | 434 | 445 | 447 | 457 | 469 | 471 | 473 |
| 144 | R114 | 348 | 350 | 364 | 378 | 388 | 390 | 398 | 399 | 405 | 418 | 419 | 428 | 433 | 434 | 435 | 446 | 448 | 458 | 470 | 472 | 474 |
| 155 | R115 | 359 | 361 | 375 | 389 | 399 | 401 | 409 | 410 | 416 | 429 | 430 | 439 | 444 | 445 | 446 | 457 | 459 | 469 | 481 | 483 | 485 |
| 157 | R116 | 361 | 363 | 377 | 391 | 401 | 403 | 411 | 412 | 418 | 431 | 432 | 441 | 446 | 447 | 448 | 459 | 461 | 471 | 483 | 485 | 487 |
| 167 | R117 | 371 | 373 | 387 | 401 | 411 | 413 | 421 | 422 | 428 | 441 | 442 | 451 | 456 | 457 | 458 | 469 | 471 | 481 | 493 | 495 | 497 |
| 179 | R118 | 383 | 385 | 399 | 413 | 423 | 425 | 433 | 434 | 440 | 453 | 454 | 463 | 458 | 469 | 470 | 481 | 483 | 493 | 505 | 507 | 509 |
| 181 | R119 | 385 | 387 | 401 | 415 | 425 | 427 | 435 | 436 | 442 | 455 | 456 | 465 | 470 | 471 | 472 | 483 | 485 | 495 | 507 | 509 | 511 |
| 183 | R120 | 387 | 389 | 403 | 417 | 427 | 429 | 437 | 438 | 444 | 457 | 458 | 467 | 472 | 472 | 474 | 485 | 487 | 497 | 509 | 511 | 513 |
| | | 1 | 3 | 9 | 4 | 4 | 2 | 1 | 3 | 1 | 1 | 2 | 0 | 1 | 0 | 1 | 2 | 1 | 1 | 1 | 1 | 0 |

What is claimed is:

1. A method of identifying predicted or actual structures of two or more members of a chemical or physical library, comprising:

(a) providing a logical matrix comprising virtual masses of members of a library produced by chemical or physical transformations of an initial set of chemical or physical members, wherein at least one group of the virtual masses comprises masses that correspond to library members having a shared chemical history and wherein two or more of the virtual masses are identical to one another;

(b) correlating molecular mass measurements of two or more chemical or physical library members having a shared chemical history with two or more virtual masses in the logical matrix to identify one or more groups of virtual masses that most likely describe chemical or physical transformations undergone by the two or more chemical or physical library members; and, (c) identifying the predicted or actual structures of the two or more chemical or physical library members within the one or more identified groups based on the molecular mass measurements.

2. The method of claim 1, wherein the method is completely or partially computer implemented.

3. The method of claim 1, wherein the library comprises a combinatorial chemical library.

4. The method of claim 1, wherein individual masses of the initial set of chemical or physical members are known.

5. The method of claim 1, wherein individual masses of the initial set of chemical or physical members are unknown.

6. The method of claim 1, wherein the chemical or physical transformations comprise multiple chemical or physical transformations to the initial set of chemical or physical members.

7. The method of claim 1, wherein the chemical or physical transformations comprise additions of one or more common scaffolds to each of the initial set of chemical or physical members.

8. The method of claim 1, wherein a mass of each member of the initial set of chemical or physical members is determined using a mass spectrometer.

9. The method of claim 1, wherein the molecular mass measurements comprises mass spectrometric measurements.

10. The method of claim 1, wherein the two or more chemical or physical library members are members of a synthesized set of compounds.

11. The method of claim 1, further comprising synthesizing the two or more chemical or physical library members, which library members correspond to all or a portion of the virtual masses represented in the logical matrix.

12. The method of claim 1, wherein multiple groups of the virtual masses comprise masses that correspond to library members having shared chemical histories.

13. The method of claim 1, wherein the one or more groups of virtual masses describe the chemical or physical transformations undergone by the two or more chemical or physical library members in (b).

14. The method of claim 1, wherein correlations in (b) account for one or more mass defects of reaction.

15. The method of claim 1, wherein (b) comprises:
(i) determining the molecular mass measurements for each of x members of a set of chemical or physical library members, wherein x is at least two, and wherein each of the x members is derived from a member of the initial set of chemical or physical members and comprises a shared chemical history with all other x members;
(ii) subtracting a cumulative total mass of all members of the initial set of chemical or physical members from a cumulative total mass of all x members of the set of chemical or physical library members to determine a cumulative total mass change for the set of chemical or physical library members;
(iii) dividing the cumulative total mass change by x to thereby determine a mass change for each of the x members of the set of chemical or physical library members; and,
(iv) subtracting the mass change of (iii) from each of the molecular mass measurements of (i) to thereby identify each member in the initial set of chemical or physical members corresponding to each individual x member of the set of chemical or physical library members.

16. The method of claim 1, wherein (a) comprises solving a simultaneous system of equations to provide one or more values in the logical matrix.

17. The method of claim 16, wherein solving the simultaneous system of equations comprises solving for one or more masses of one or more members of the initial set of chemical or physical members.

18. The method of claim 16, wherein solving the simultaneous system of equations comprises solving for one or more of: at least one mass of at least one member of the set of chemical or physical library members, at least one mass of at least one of the initial set of chemical or physical members, or at least one member of a set of expected mass changes.

19. The method of claim 1, wherein (a) comprises calculating individual masses for each member of the logical matrix by separately summing masses for each member of the initial set of chemical or physical members with each mass in a set of expected mass changes, wherein each calculated individual mass is assigned to one of m groups, m corresponding to a total number of individual mass changes in the set of expected mass changes, and wherein each of the m groups comprises ii members, n corresponding to a total number of members in the initial set of chemical or physical members.

20. The method of claim 19, wherein the set of expected mass changes comprises a set of virtual mass changes calculated by separately subtracting masses for each member of the initial set of chemical or physical members from each mass in the set of chemical or physical library members.

21. The method of claim 19, wherein (b) comprises:
(i) matching a selected mass from the set of chemical or physical library members with all identical calculated masses and excluding any of the m groups lacking a member n comprising a mass identical to the selected mass from further consideration to reduce a number of m groups available for subsequent consideration;
(ii) repeating (i) at least once, wherein each repeated (i) comprises matching a different selected mass from the set of chemical or physical library members with all the identical calculated masses that remain in the reduced number of m groups from an immediately preceding (i) and excluding any of the reduced number of m groups lacking an n member with a mass identical to the different selected mass from further consideration to further reduce the number of in groups available for subsequent consideration, thereby:
(1) identifying a single m group which indicates that matched masses from the set of chemical or physical library members have a shared chemical history;
(2) identifying more than one m group for further consideration which indicates that insufficient data exists for an unambiguous determination of whether masses selected from the set of chemical or physical library members have a shared chemical history; or,
(3) identifying no m group for further consideration which indicates that masses selected from the set of chemical or physical library members originate from materials lacking a shared chemical history.

22. The method of claim 19, further comprising assigning each of the m groups a P variable, wherein each P variable is initially zero.

23. The method of claim 22, wherein (b) comprises:
(i) matching a selected mass from the set of chemical or physical library members with identical masses in each of the m groups, wherein the P variable for an m group is increased by one when the selected mass matches at least one value therein;
(ii) repeating (i) for each remaining value in the set of chemical or physical library members; and,
(iii) determining which one or more m groups have highest P variables, thereby identifying one or more mass changes from the set of expected mass changes best fitting the set of chemical or physical library members, and all paired values in the initial set of chemical or physical members and the set of chemical or physical library members originating from materials with a shared chemical history.

24. A method of determining predicted or actual structures of two or more members of a chemical or physical library, comprising:
(a) providing a logical matrix comprising virtual masses of members of a library produced by chemical or physical transformations of an initial set of chemical or physical members, wherein one or more groups of the virtual masses comprise masses that correspond to library members having a shared chemical history and wherein two or more of the virtual masses are identical to one another;
(b) providing at least one set of chemical or physical library members corresponding to two or more members of the library, wherein the at least one set of chemical or physical library members comprises unknown structures or is non-arrayed; and,
(c) correlating mass measurements of two or more of the chemical or physical library members to two or more virtual masses in one of the one or more groups, thereby determining the predicted or actual structures of the two or more chemical or physical library members.

25. A system for identifying predicted or actual structures for two or more members of a chemical or physical library, comprising:
(a) at least one computer comprising a database having a logical matrix comprising virtual masses of members of a library produced by chemical or physical transformations of an initial set of chemical or physical members, wherein at least one group of the virtual masses comprises masses that correspond to library members having a shared chemical history and wherein two or more of the virtual masses are identical to one another; and,
(b) system software comprising one or more logic instructions for:
(i) correlating molecular mass measurements of two or more chemical or physical library members having a shared chemical history wit two or more virtual masses in the logical matrix to identify one or more groups of virtual masses that most likely describe chemical or physical transformations undergone by the two or more chemical or physical library members; and,
(ii) identifying the predicted or actual structures of the two or more chemical or physical library members within the one or more identified groups based on the molecular mass measurements.

26. The system of claim 25, wherein the one or more groups of virtual masses describe the chemical or physical transformations undergone by the two or more chemical or physical library members in (b).

27. The system of claim 25, wherein correlations in (i) account for one or more mass defects of reaction.

28. The system of claim 25, further comprising a mass spectrometer operably connected to the at least one computer which provides the molecular mass measurements to be correlated.

29. The system of claim 25, wherein the system software is stored on one or more of: a CD-ROM, a floppy disk, a tape, a flash memory device or component, a system memory device or component, a hard drive, or a data signal embodied in a carrier wave.

30. The system of claim 25, further comprising a handling system operably connected to the at least one computer, which handling system directs translocation and synthesis of the chemical or physical library members.

31. The system of claim 30, wherein the handling system comprises at least one robotic armature.

32. The system of claim 30, wherein the handling system comprises a solid support handler.

33. The system of claim 32, wherein the solid support handler comprises a bead handler or a bead container handler.

34. A computer program product comprising a computer readable medium having one or more logic instructions for
(a) correlating molecular mass measurements of two or more chemical or physical library members having a shared chemical history with two or more virtual masses in a logical matrix to identity one or more groups of virtual masses that most likely describe chemical or physical transformations undergone by the two or more chemical or physical library members, wherein two or more of the virtual masses are identical to one another; and,
(b) identifying predicted or actual structures of the two or more chemical or physical library members within the one or more identified groups based on the molecular mass measurements.

35. The computer program product of claim 34, wherein correlations account for one or more mass defects of reaction.

36. The computer program product of claim 34, wherein the computer readable medium Comprises one or more of: a CD-ROM, a floppy disk, a tape, a flash memory device or component, a system memory device or component, a hard drive, or a data signal embodied in a carrier wave.

37. A method of identifying a predicted or actual structure of a chemical or physical library member, comprising:
(a) providing a logical matrix comprising virtual masses of members of a library produced by chemical or physical transformations of an initial set of chemical or physical members, wherein at least one group of the virtual masses comprises masses that correspond to library members having a shared chemical history;
(b) correlating a molecular mass measurement of the chemical or physical library member with two or more virtual masses in the logical matrix to identify one or more groups of virtual masses that most likely describe a chemical or physical transformation undergone by the chemical or physical library member; and,
(c) identifying the predicted or actual structure of the chemical or physical library member within the one or more identified groups based on the molecular mass measurement.

38. The method of claim 37, wherein the method is completely or partially computer implemented.

39. The method of claim 37, wherein the library comprises a combinatorial chemical library.

40. The method of claim 37, wherein individual masses of the initial set of chemical or physical members are known.

41. The method of claim 37, wherein individual masses of the initial set of chemical or physical members are unknown.

42. The method of claim 37, wherein a mass of each member of the initial set of chemical or physical members is determined using a mass spectrometer.

43. The method of claim 37, wherein (a) comprises solving a simultaneous system of equations to provide one or more values in the logical matrix.

44. The method of claim 43, wherein solving the simultaneous system of equations comprises solving for one or more masses of one or more members of the initial set of chemical or physical members.

45. The method of claim 43, wherein solving the simultaneous system of equations comprises solving for one or more of: at least one mass of at least one member of the set of chemical or physical library members, at least one mass of at least one of the initial set of chemical or physical members, or at least one member of a set of expected mass changes.

46. The method of claim 37, wherein (b) further comprises correlating molecular mass measurements of one or more additional chemical or physical library members with one or more of the virtual masses in the logical matrix to further identify the one or more groups of virtual masses that most likely describe chemical or physical transformations undergone by the chemical or physical library member and the additional chemical or physical library members.

47. The method of claim 46, wherein the chemical or physical library member and the additional chemical or physical library members have a shared chemical history.

48. The method of claim 46, wherein (c) further comprises identifying the predicted or actual structures of the additional chemical or physical library members within the one or more identified groups based on the molecular mass measurements.

49. The method of claim 46, wherein the chemical or physical transformations comprise multiple chemical or physical transformations to the initial set of chemical or physical members.

50. The method of claim 46, wherein the molecular mass measurements comprise mass spectrometric measurements.

51. The method of claim 46, wherein the chemical or physical transformations comprise additions of one or more common scaffolds to each of the initial set of chemical or physical members.

52. The method of claim 46, wherein the chemical or physical library member and the additional chemical or physical library members are members of a synthesized set of compounds.

53. The method of claim 46, further comprising synthesizing the chemical or physical library member and the additional chemical or physical library members, which library members correspond to all or a portion of the virtual masses represented in the logical matrix.

54. The method of claim 46, wherein multiple groups of the virtual masses comprise masses that correspond to library members having shared chemical histories.

55. The method of claim 46, wherein the one or more groups of virtual masses describe the chemical or physical transformations undergone by the chemical or physical library member and the additional chemical or physical library members in (b).

56. The method of claim 46, wherein correlations in (b) account for one or more mass defects of reaction.

57. The method of claim 46, wherein (b) comprises:
(i) determining the molecular mass measurements for each of x members of a set of chemical or physical library members, wherein x is at least two, and wherein each of the x members is derived from a member of the initial set of chemical or physical members and comprises a shared chemical history with all other x members;

(ii) subtracting a cumulative total mass of all members of the initial set of chemical or physical members from a cumulative total mass of all x members of the set of chemical or physical library members to determine a cumulative total mass change for the set of chemical or physical library members;

(iii) dividing the cumulative total mass change by x to thereby determine a mass change for each of the x members of the set of chemical or physical library members; and, (iv) subtracting the mass change of (iii) from each of the molecular mass measurements of (i) to thereby identify each member in the initial set of chemical or physical members corresponding to each individual x member of the set of chemical or physical library members.

58. The method of claim 46, wherein (a) comprises calculating individual masses for each member of the logical matrix by separately summing masses for each member of the initial set of chemical or physical members with each mass in a set of expected mass changes, wherein each calculated individual mass is assigned to one of m groups, m corresponding to a total number of individual mass changes in the set of expected mass changes, and wherein each of the m groups comprises n members, n corresponding to a total number of members in the initial set of chemical or physical members.

59. The method of claim 58, wherein the set of expected mass changes comprises a set of virtual mass changes calculated by separately subtracting masses for each member of the initial set of chemical or physical members from each mass in the set of chemical or physical library members.

60. The method of claim 58, wherein (b) comprises:
(i) matching a selected mass from the set of chemical or physical library members with all identical calculated masses and excluding any of the m groups lacking a member n comprising a mass identical to the selected mass from further consideration to reduce a number of m groups available for subsequent consideration;

(ii) repeating (i) at least once, wherein each repeated (i) comprises matching a different selected mass from the set of chemical or physical library members with all the identical calculated masses that remain in the reduced number of m groups from an immediately preceding (i) and excluding any of the reduced number of m groups lacking an n member with a mass identical to the different selected mass from further consideration to further reduce the number of in groups available for subsequent consideration, thereby:
(1) identifying a single m group which indicates that matched masses from the set of chemical or physical library members have a shared chemical history;
(2) identifying more than one m group for further consideration which indicates that insufficient data exists for an unambiguous determination of whether masses selected from the set of chemical or physical library members have a shared chemical history; or,
(3) identifying no m group for further consideration which indicates that masses selected from the set of chemical or physical library members originate from materials lacking a shared chemical history.

61. The method of claim 58, further comprising assigning each of the m groups a P variable, wherein each P variable is initially zero.

62. The method of claim 61, wherein (b) comprises:
(i) matching a selected mass from the set of chemical or physical library members with identical masses in each of the m groups, wherein the P variable for an m group is increased by one when the selected mass matches at least one value therein;

(ii) repeating (i) for each remaining value in the set of chemical or physical library members; and, (iii) determining which one or more m groups have highest P variables, thereby identifying one or more mass changes from the set of expected mass changes best fitting the set of chemical or physical library members, and all paired values in the initial set of chemical or physical members and the set of chemical or physical library members originating from materials with a shared chemical history.

63. A method of determining predicted or actual structures of two or more members of a chemical or physical library, comprising:

(a) providing a logical matrix comprising virtual masses of members of a library produced by chemical or physical transformations of an initial set of chemical or physical members, wherein one or more groups of the virtual masses comprise masses that correspond to library members having a shared chemical history;

(b) providing at least one set of chemical or physical library members corresponding to two or more members of the library, wherein the at least one set of chemical or physical library members comprises unknown structures or is non-arrayed; and, (c) correlating mass measurements of two or more of the chemical or physical library members to three or more virtual masses in one of the one or more groups, wherein at least one of the mass measurements correlates to two or more of the virtual masses in the logical matrix, thereby determining the predicted or actual structures of the two or more chemical or physical library members.

64. A system for identifying a predicted or actual structure of a chemical or physical library member, comprising:

(a) at least one computer comprising a database having a logical matrix comprising virtual masses of members of a library produced by chemical or physical transformations of an initial set of chemical or physical members, wherein at least one group of the virtual masses comprises masses that correspond to library members having a shared chemical history; and, (b) system software comprising one or more logic instructions for:

(i) correlating a molecular mass measurement of the chemical or physical library member with two or more virtual masses in the logical matrix to identify one or more groups of virtual masses that most likely describe a chemical or physical transformation undergone by the chemical or physical library member; and, (ii) identifying the predicted or actual structure of the chemical or physical library member within the one or more identified groups based on the molecular mass measurement.

65. The system of claim 64, wherein (i) further correlates molecular mass measurements of one or more additional chemical or physical library members with one or more of the virtual masses in the logical matrix to further identify the one or more groups of virtual masses that mast likely describe chemical or physical transformations undergone by the chemical or physical library member and the additional chemical or physical library members.

66. The system of claim 65, wherein the chemical or physical library member and the additional chemical or physical library members have a shared chemical history.

67. The system of claim 65, wherein (ii) further identifies the predicted or actual structures of the additional chemical or physical library members within the one or more identified groups based on the molecular mass measurements.

68. The system of claim 65, wherein the one or more groups of virtual masses describe the chemical or physical transformations undergone by the chemical or physical library member and the additional chemical or physical library members in (i).

69. The system of claim 65, wherein correlations in (i) account for one or more mass defects of reaction.

70. The system of claim 65, further comprising a mass spectrometer operably connected to the at least one computer which provides the molecular mass measurements to be correlated.

71. The system of claim 65, wherein the system software is stored on one or more of: a CD-ROM, a floppy disk, a tape, a flash memory device or component, a system memory device or component, a hard drive, or a data signal embodied in a carrier wave.

72. The system of claim 65, further comprising a handling system operably connected to the at least one computer, which handling system directs translocation and synthesis of the chemical or physical library members.

73. The system of claim 72, wherein the handling system comprises at least one robotic armature.

74. The system of claim 72, wherein the handling system comprises a solid support handler.

75. The system of claim 74, wherein the solid support handler comprises a bead handler or a bead container handler.

76. A computer program product comprising a computer readable medium having one or more logic instructions for (a) correlating a molecular mass measurement of a chemical or physical library member with two or more virtual masses in a logical matrix to identify one or more groups of virtual masses that most likely describe a chemical or physical transformation undergone by the chemical or physical library member; and, (b) identifying the predicted or actual structure of the chemical or physical library member within the one or more identified groups based on the molecular mass measurement.

77. The computer program product of claim 76, wherein (a) further correlates molecular mass measurements of one or more additional chemical or physical library members with one or more of the virtual masses in the logical matrix to further identify the one or more groups of virtual masses tat most likely describe chemical or physical transformations undergone by the chemical or physical library member and the additional chemical or physical library members.

78. The computer program product of claim 77, wherein the chemical or physical library member and the additional chemical or physical library members have a shared chemical history.

79. The computer program product of claim 77, wherein (b) further identifies the predicted or actual structures of the additional chemical or physical library members within the one or more identified groups based on the molecular mass measurements.

80. The computer program product of claim 77, wherein correlations account for one or more mass defects of reaction.

81. The computer program product of claim 77, wherein the computer readable medium comprises one or more of: a CD-ROM, a floppy disk, a tape, a flash memory device or component, a system memory device or component, a hard drive, or a data signal embodied in a carrier wave.

* * * * *

UNITED STATES PATENT AND TRADEMARK OFFICE
CERTIFICATE OF CORRECTION

PATENT NO. : 6,625,546 B2  
DATED : September 23, 2003  
INVENTOR(S) : Sepetov et al.

It is certified that error appears in the above-identified patent and that said Letters Patent is hereby corrected as shown below:

Column 40,
Line 23, delete "ii" and insert -- n --
Line 47, delete "in" and insert -- m --

Column 41,
Line 50, delete "wit" and insert -- with --

Column 42,
Line 36, delete "Comprises" and insert -- comprises --

Column 44,
Line 48, delete "in" and insert -- m --

Column 45,
Line 62, delete "mast" and insert -- most --

Column 46,
Line 49, delete "tat" and insert -- that --

Signed and Sealed this

Second Day of December, 2003

JAMES E. ROGAN
*Director of the United States Patent and Trademark Office*